(12) United States Patent
Ushikura et al.

(10) Patent No.: US 11,766,227 B2
(45) Date of Patent: Sep. 26, 2023

(54) RADIATION DETECTOR, RADIOGRAPHIC IMAGING APPARATUS, AND METHOD OF MANUFACTURING RADIATION DETECTOR

(71) Applicant: FUJIFILM CORPORATION, Tokyo (JP)

(72) Inventors: Shinichi Ushikura, Kanagawa (JP); Munetaka Kato, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 17/822,131

(22) Filed: Aug. 25, 2022

(65) Prior Publication Data

US 2022/0409153 A1 Dec. 29, 2022

Related U.S. Application Data

(63) Continuation of application No. PCT/JP2021/006938, filed on Feb. 24, 2021.

(30) Foreign Application Priority Data

Mar. 5, 2020 (JP) .................................. 2020-038171

(51) Int. Cl.
*G01T 1/20* (2006.01)
*A61B 6/00* (2006.01)

(52) U.S. Cl.
CPC .............. *A61B 6/4208* (2013.01); *G01T 1/20* (2013.01)

(58) Field of Classification Search
CPC ... A61B 6/4208; A61B 6/4429; A61B 6/4225; A61B 6/4405; A61B 6/42; G01T 1/20; G01T 1/2002; G01T 1/2006
See application file for complete search history.

(56) References Cited

U.S. PATENT DOCUMENTS

2009/0004425 A1 1/2009 Lehman et al.
2010/0102236 A1* 4/2010 Inoue ................... G01T 1/2018
250/361 R (Continued)

FOREIGN PATENT DOCUMENTS

JP 2009-113470 A 5/2009
JP 2011-247826 A 12/2011

(Continued)

OTHER PUBLICATIONS

English language translation of the following: Office action dated May 23, 2023 from the JPO in a Japanese patent application No. 2022-505148 corresponding to the instant patent application.

(Continued)

*Primary Examiner* — Kiho Kim
(74) *Attorney, Agent, or Firm* — SOLARIS Intellectual Property Group, PLLC

(57) ABSTRACT

A radiation detector includes a sensor substrate, a conversion layer, and a reinforcing substrate. In the sensor substrate, a plurality of pixels for accumulating electric charges generated in response to light converted from radiation are formed on a pixel region of a flexible base material. The conversion layer is provided on a first surface of the base material on which the pixels are provided and converts radiation into light. The reinforcing substrate is provided on a surface of the conversion layer opposite to a surface on the base material side and includes a porous layer having a plurality of through-holes to reinforce the stiffness of the base material.

18 Claims, 25 Drawing Sheets

(56) References Cited

U.S. PATENT DOCUMENTS

| | | | |
|---|---|---|---|
| 2012/0219114 A1 | 8/2012 | Iwakiri et al. | |
| 2015/0369930 A1 | 12/2015 | Mruthyunjaya et al. | |
| 2016/0282479 A1* | 9/2016 | Tanino | G01T 1/2002 |
| 2021/0003515 A1 | 1/2021 | Ushikura et al. | |
| 2021/0003722 A1 | 1/2021 | Kato et al. | |
| 2021/0096271 A1 | 4/2021 | Okada et al. | |

FOREIGN PATENT DOCUMENTS

| | | |
|---|---|---|
| JP | 2012-173275 A | 9/2012 |
| JP | 2014-081363 A | 5/2014 |
| WO | 2019/181569 A1 | 9/2019 |

OTHER PUBLICATIONS

International Search Report issued in International Application No. PCT/JP2021/006938 dated May 18, 2021.
Written Opinion of the ISA issued in International Application No. PCT/JP2021/006938 dated May 18, 2021.

* cited by examiner

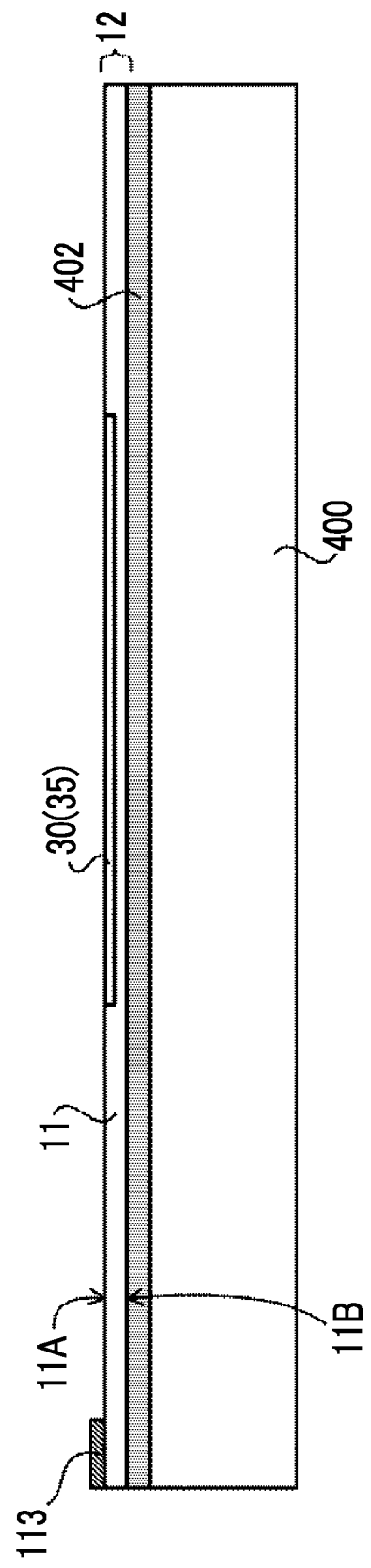

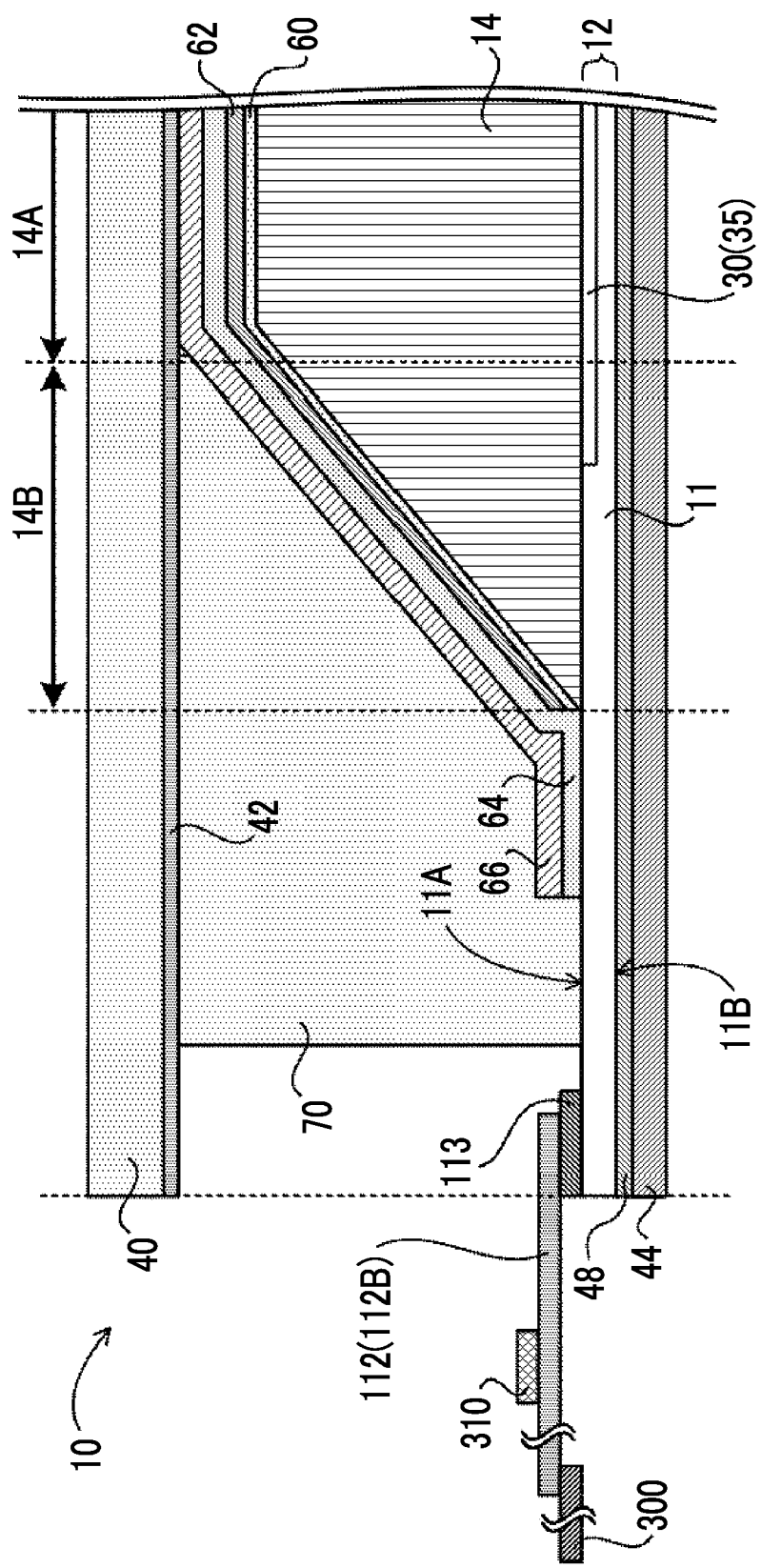

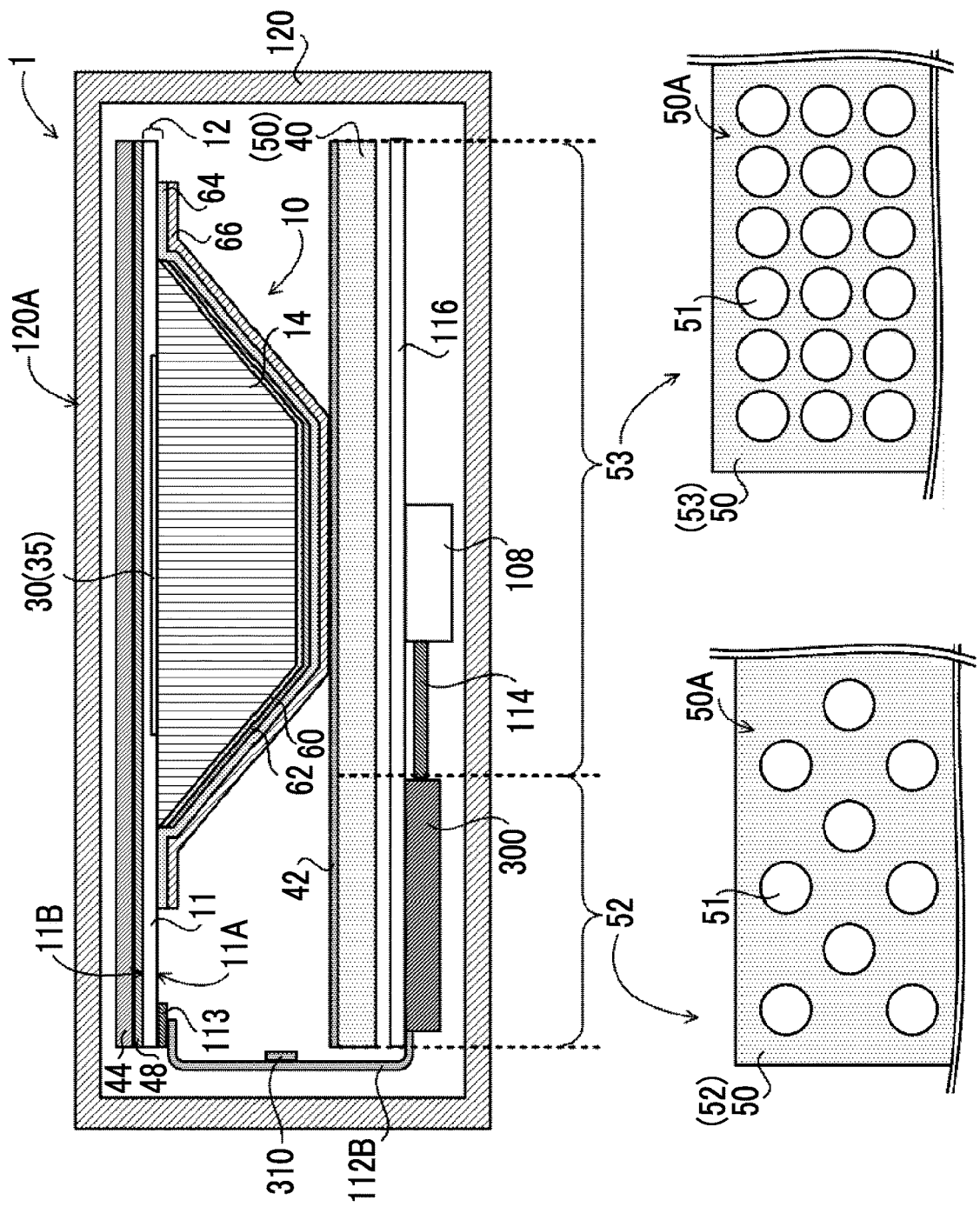

RADIATION DETECTOR, RADIOGRAPHIC IMAGING APPARATUS, AND METHOD OF MANUFACTURING RADIATION DETECTOR

CROSS-REFERENCE TO RELATED APPLICATIONS

This application is a continuation application of International Application No. PCT/JP2021/006938, filed Feb. 24, 2021, the disclosure of which is incorporated herein by reference in its entirety. Further, this application claims priority from Japanese Patent Application No. 2020-038171, filed on Mar. 5, 2020, the disclosure of which is incorporated herein by reference in its entirety.

BACKGROUND

1. Technical Field

The present disclosure relates to a radiation detector, a radiographic imaging apparatus, and a method of manufacturing the radiation detector.

2. Description of the Related Art

In the related art, radiographic imaging apparatuses that perform radiographic imaging for medical diagnosis have been known. A radiation detector for detecting radiation transmitted through a subject and generating a radiographic image is used for such radiographic imaging apparatuses.

As the radiation detector, there is one comprising a conversion layer, such as a scintillator, which converts radiation into light, and a substrate in which a plurality of pixels, which accumulate electric charges generated in response to light converted in the conversion layer, are provided. As the base material of a sensor substrate of such a radiation detector, one formed of a flexible base material is known. Additionally, by using the flexible base material, there is a case where the weight of the radiographic imaging apparatuses can be reduced and imaging of the subject becomes easy.

Meanwhile, in a case where a load, an impact, or the like is applied to a radiographic imaging apparatus, the substrate using the flexible base material is easily deflected. Therefore, in order to suppress the influence of the impact or the like on the radiation detector, the technique of increasing the bending stiffness of the radiation detector is known.

For example, JP2012-173275A describes a technique of providing a reinforcing member serving as a reinforcing substrate on a side, opposite to a scintillator side, of a thin film unit that detects fluorescence as an electrical signal. Additionally, for example, JP2014-081363A describes a technique of bonding a reinforcing substrate to a radiation incidence side of a photoelectric conversion panel or a side opposite to the radiation incidence side.

SUMMARY

In the techniques described in JP2012-173275A and JP2014-081363A, the bending stiffness of the radiation detectors can be increased as described above, but the weight of the entire radiation detectors is increased due to the reinforcing substrate. For that reason, in the techniques described in Patent Documents 1 and 2, there is a case where the effect of reducing the weight of the radiographic imaging apparatus is not sufficiently obtained by using the flexible base material.

The present disclosure provides a radiation detector, a radiographic imaging apparatus, and a method of manufacturing a radiation detector having high bending stiffness and reduced weight.

A radiation detector of a first aspect of the present disclosure comprises a substrate in which a plurality of pixels for accumulating electric charges generated in response to light converted from radiation is formed in a pixel region of a flexible base material; a conversion layer that is provided on a surface side of the base material provided with the pixels and converts the radiation into the light; and a reinforcing substrate that is provided on a surface of the conversion layer opposite to a surface on a base material side and includes a porous layer having a plurality of through-holes to reinforce a stiffness of the base material.

Additionally, a radiation detector of a second aspect of the present disclosure is the radiation detector of the first aspect in which each of the plurality of through-holes has an opening diameter of 0.5 mm or more and 50 mm or less, a pitch of 1 mm or more and 50 mm or less, and an opening ratio of 10% or more and 50% or less.

Additionally, a radiation detector of a third aspect of the present disclosure is the radiation detector of the first or second aspect in which the porous layer has the plurality of through-holes having a hexagonal opening.

Additionally, a radiation detector of a fourth aspect of the present disclosure is the radiation detector of the third aspect in which the porous layer has a honeycomb structure.

Additionally, a radiation detector of a fifth aspect of the present disclosure is the radiation detector of the first aspect in which the porous layer has a porous structure having a porosity of 15% or more and 50% or less and a pore diameter of 0.3 μm or more and 5 mm or less.

Additionally, a radiation detector of a sixth aspect of the present disclosure is the radiation detector of the first aspect in which the porous layer has a flute structure in which an extension direction of a flute is an in-plane direction of the reinforcing substrate.

Additionally, a radiation detector of a seventh aspect of the present disclosure is the radiation detector of the sixth aspect in which a pitch of the flute structure is at least a thickness of the flute structure and no more than three times the thickness.

Additionally, the radiation detector of an eighth aspect of the present disclosure is the radiation detector of any one of the first to seventh aspects in which a material of the porous layer includes at least one of carbon fiber reinforced plastic (CFRP), carbon fiber reinforced thermo plastics (CFRTP), polyvinyl chloride (PVC), polyethylene terephthalate (PET), polypropylene (PP), polyethylene (PE), aluminum, or magnesium.

Additionally, a radiation detector of a ninth aspect of the present disclosure is the radiation detector of any one of the first to seventh aspects in which a main component of a material of the porous layer is carbon fiber reinforced plastic (CFRP).

Additionally, a radiation detector of a tenth aspect of the present disclosure is the radiation detector of any one of the first to ninth aspects in which the through-holes of the porous layer have different densities in each region of a plurality of regions lined up along the surface of the base material provided with the pixels.

Additionally, a radiation detector of an eleventh aspect of the present disclosure is the radiation detector of the tenth aspect in which the density of the through-holes in a region corresponding to a position where a circuit unit for reading the electric charges accumulated in the pixels is provided is smaller than the densities of the through-holes in the other regions.

Additionally, a radiation detector of a twelfth aspect of the present disclosure is the radiation detector of the tenth aspect in which the density of the through-holes in a region corresponding to a power source unit that supplies power to a circuit unit for reading the electric charges accumulated in the pixels is provided is larger than the densities of the through-holes in the other regions.

Additionally, a radiation detector of a thirteenth aspect of the present disclosure is the radiation detector of any one of the first to twelfth aspects in which the reinforcing substrate includes a laminated body in which a plurality of the porous layers are laminated.

Additionally, a radiation detector of a fourteenth aspect of the present disclosure is the radiation detector of any one of the first to thirteenth aspects in which the porous layer has a protective plate provided on at least one surface of a surface on a conversion layer side and a surface opposite to the conversion layer.

Additionally, a radiation detector of a fifteenth aspect of the present disclosure is the radiation detector of any one of the first to first to fourteenth aspects further comprising an antistatic layer that is provided on a surface of the base material opposite to the surface provided with the pixels.

Additionally, a radiation detector of a sixteenth aspect of the present disclosure is the radiation detector of the fifteenth aspect in which the antistatic layer is a laminated film of a resin film and a metal film.

Additionally, a radiographic imaging apparatus according to a seventeenth aspect of the present disclosure comprises a radiation detector of the present disclosure; and a circuit unit for reading out the electric charges accumulated in the plurality of pixels.

Additionally, a method of manufacturing a radiation detector according to an eighteenth aspect of the present disclosure comprises a step of providing a flexible base material on a support body and forming a substrate in which a plurality of pixels that accumulate electric charges generated in response to light converted from radiation are provided in a pixel region of a first surface of the base material; a step of forming a conversion layer for converting the radiation into the light on a surface side of the base material provided with the pixels; a step of providing a reinforcing substrate including a porous layer having a plurality of through-holes on a surface of the conversion layer opposite to a surface on the base material side to reinforce a stiffness of a base material; and a step of peeling the substrate from the support body.

Additionally, a method of manufacturing a radiation detector according to an eighteenth aspect of the present disclosure is the method of manufacturing a radiation detector according to the nineteenth aspect in which the step of peeling the substrate from the support body is performed after the reinforcing substrate is provided on the substrate.

According to the present disclosure, the bending stiffness is high and the heat resistance can be improved.

BRIEF DESCRIPTION OF THE DRAWINGS

Exemplary embodiments according to the technique of the present disclosure will be described in detail based on the following figures, wherein:

FIG. 10A is a view for explaining an example of a method of manufacturing the radiographic imaging apparatus of the embodiment, FIG. 13 is a cross-sectional view taken along line A-A of an example of a radiation detector of Modification Example 2, FIG. 14A is a diagram for explaining an example of a porous layer of Modification Example 3.

DETAILED DESCRIPTION

Hereinafter, embodiments of the present disclosure will be described in detail with reference to the drawings. In addition, the present embodiments do not limit the present disclosure.

The radiation detector of the present embodiment has a function of detecting radiation transmitted through a subject to output image information representing a radiographic image of the subject. The radiation detector of the present embodiment comprises a sensor substrate and a conversion layer that converts radiation into light (refer to a sensor substrate 12 and a conversion layer 14 of the radiation detector 10 in FIG. 3). The sensor substrate 12 of the present embodiment is an example of a substrate of the present disclosure.

Figure 1:
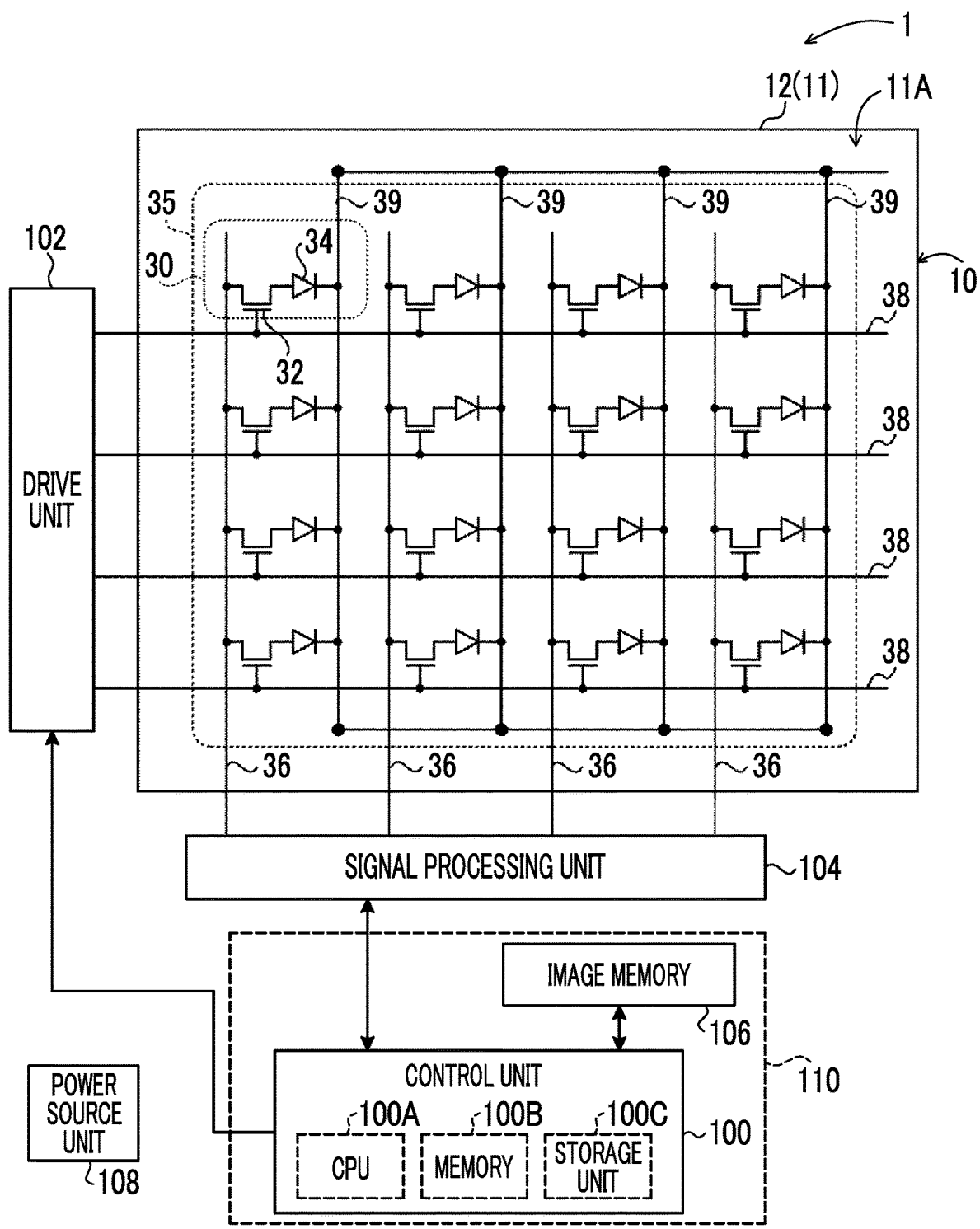
FIG. 1 is a block diagram showing an example of the configuration of major parts of an electrical system in a radiographic imaging apparatus of an embodiment.

First, the outline of an example of the configuration of an electrical system in a radiographic imaging apparatus of the present embodiment will be described with reference to FIG. 1. FIG. 1 is a block diagram showing an example of the configuration of major parts of the electrical system in the radiographic imaging apparatus of the present embodiment.

As shown in FIG. 1, the radiographic imaging apparatus 1 of the present embodiment comprises the radiation detector 10, a control unit 100, a drive unit 102, a signal processing unit 104, an image memory 106, and a power source unit 108. At least one of the control unit 100, the drive unit 102, or the signal processing unit 104 of the present embodiment is an example of a circuit unit of the present disclosure. Hereinafter, the control unit 100, the drive unit 102, and the signal processing unit 104 are collectively referred to as the "circuit unit".

The radiation detector 10 comprises the sensor substrate 12 and a conversion layer 14 (refer to FIG. 3) that converts radiation into light. The sensor substrate 12 comprises a flexible base material 11, and a plurality of pixels 30 provided on a first surface 11A of the base material 11. In addition, in the following description, the plurality of pixels 30 may be simply referred to as "pixels 30".

As shown in FIG. 1, each pixel 30 of the present embodiment comprises a sensor unit 34 that generates and accumulates electric charges in response to the light converted by the conversion layer 14, and a switching element 32 that reads out the electric charges accumulated in the sensor unit 34. In the present embodiment, as an example, a thin film transistor (TFT) is used as the switching element 32. For that reason, in the following description, the switching element 32 is referred to as a "TFT 32". In the present embodiment, a layer in which the pixels 30 are formed on the first surface 11A of the base material 11 is provided as a layer that is formed with the sensor unit 34 and the TFT 32 and is planarized.

The pixels 30 are two-dimensionally disposed in one direction (a scanning wiring direction corresponding to a transverse direction of FIG. 1, hereinafter referred to as a "row direction"), and a direction intersecting the row direction (a signal wiring direction corresponding to the longitudinal direction of FIG. 1, hereinafter referred as a "column direction") in a pixel region 35 of the sensor substrate 12. Although an array of the pixels 30 is shown in a simplified manner in FIG. 1, for example, 1024×1024 pixels 30 are arranged in the row direction and the column direction.

Additionally, a plurality of scanning wiring lines 38, which are provided for respective rows of the pixels 30 to control switching states (ON and OFF) of the TFTs 32, and a plurality of signal wiring lines 36, which are provided for respective columns of the pixels 30 and from which electric charges accumulated in the sensor units 34 are read, are provided in a mutually intersecting manner in the radiation detector 10. Each of the plurality of scanning wiring lines 38 is connected to the drive unit 102 via a flexible cable 112A, and thereby, a drive signal for driving the TFT 32 output from the drive unit 102 to control the switching state thereof flows through each of the plurality of scanning wiring lines 38. Additionally, the plurality of signal wiring lines 36 are electrically connected to the signal processing unit 104 via the flexible cable 112B, respectively, and thereby, electric charges read from the respective pixels 30 are output to the signal processing unit 104 as electrical signals. The signal processing unit 104 generates and outputs image data according to the input electrical signals. In addition, in the present embodiment, the term "connection" with respect to the flexible cable 112 means an electrical connection.

The control unit 100 to be described below is connected to the signal processing unit 104, and the image data output from the signal processing unit 104 is sequentially output to the control unit 100. The image memory 106 is connected to the control unit 100, and the image data sequentially output from the signal processing unit 104 is sequentially stored in the image memory 106 under the control of the control unit 100. The image memory 106 has a storage capacity capable of storing image data equivalent to a predetermined number of sheets, and whenever radiographic images are captured, image data obtained by the capturing is sequentially stored in the image memory 106.

The control unit 100 comprises a central processing unit (CPU) 100A, a memory 100B including a read only memory (ROM), a random access memory (RAM), and the like, and a nonvolatile storage unit 100C, such as a flash memory. An example of the control unit 100 is a microcomputer or the like. The control unit 100 controls the overall operation of the radiographic imaging apparatus 1.

In addition, in the radiographic imaging apparatus 1 of the present embodiment, the image memory 106, the control unit 100, and the like are formed in a control substrate 110.

Additionally, common wiring lines 39 are provided in a wiring direction of the signal wiring lines 36 at the sensor units 34 of the respective pixels 30 in order to apply bias voltages to the respective pixels 30. Bias voltages are applied to the respective pixels 30 from a bias power source by electrically connecting the common wiring lines 39 to the bias power source (not shown) outside the sensor substrate 12.

The power source unit 108 supplies electrical power to various elements and various circuits, such as the control unit 100, the drive unit 102, the signal processing unit 104, the image memory 106, and the power source unit 108. In addition, in FIG. 1, an illustration of wiring lines, which connect the power source unit 108 and various elements or various circuits together, is omitted in order to avoid complications.

Figure 2:
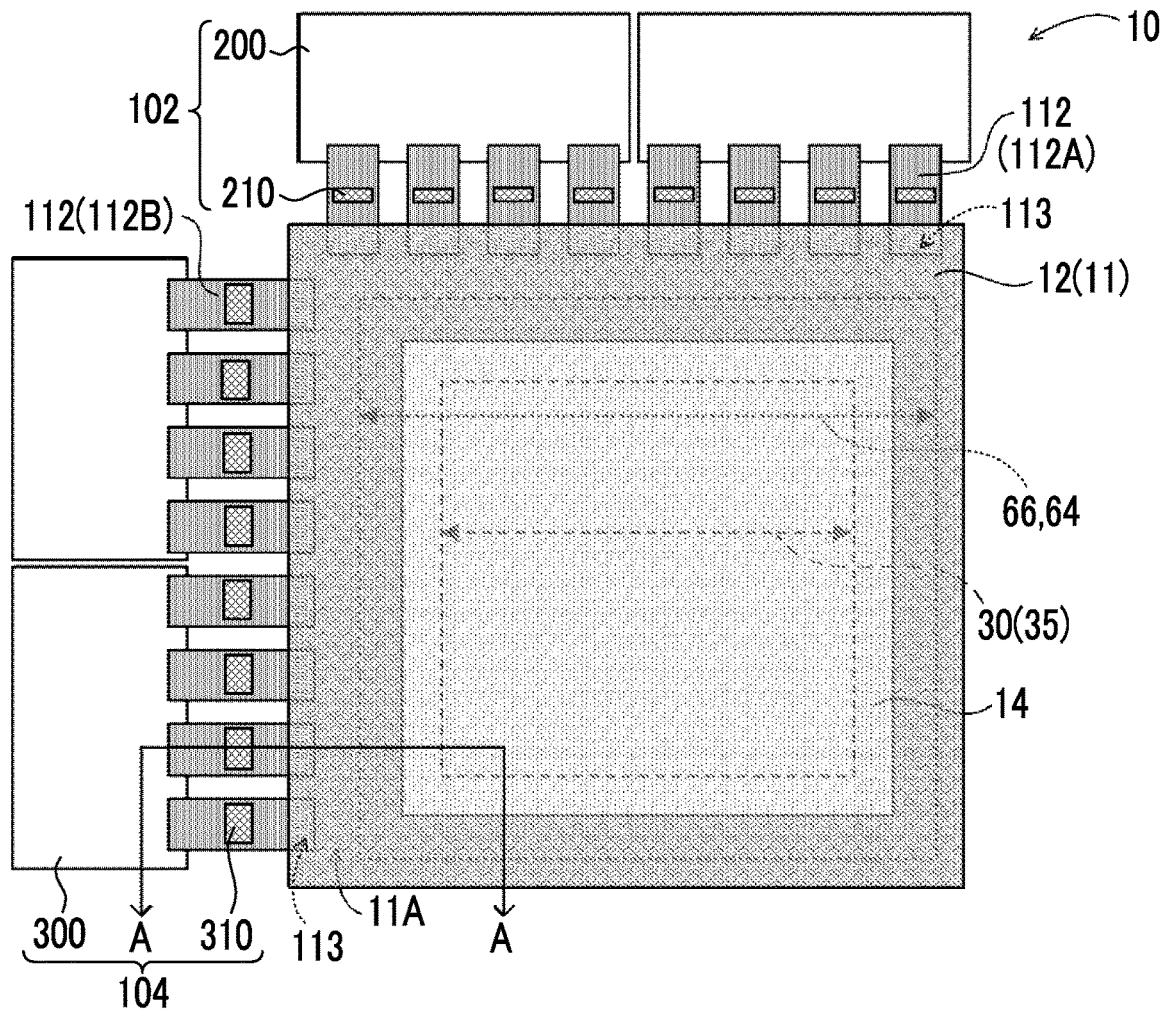
FIG. 2 is a plan view of an example of a radiation detector according to the embodiment as seen from a first surface side of a base material.
Figure 3:
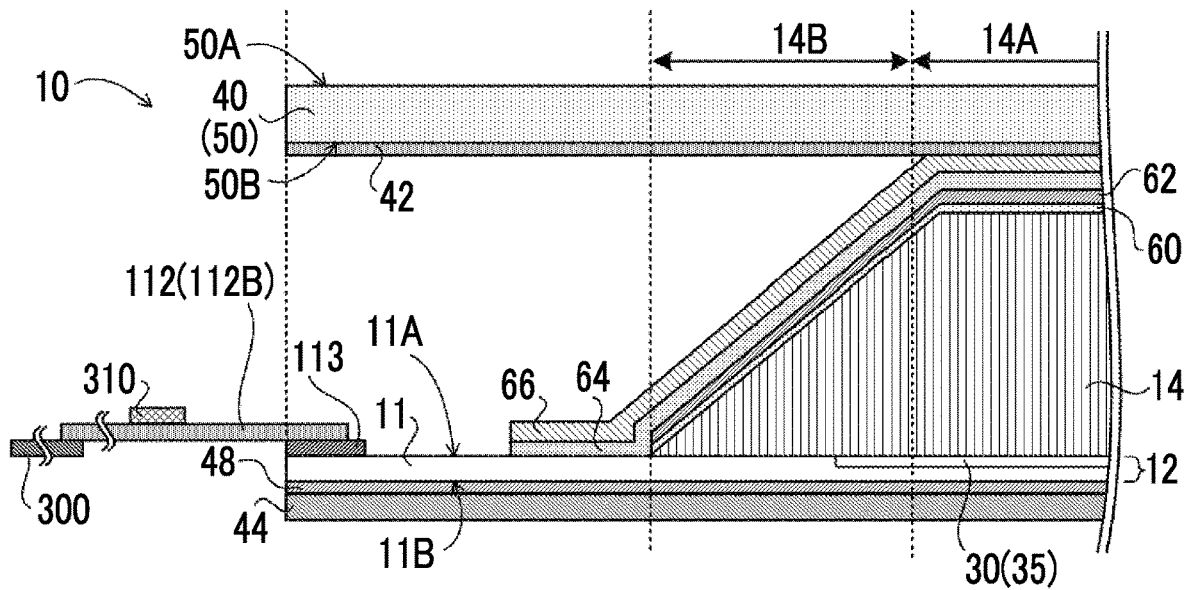
FIG. 3 is a cross-sectional view taken along line A-A of an example of the radiation detector shown in FIG. 2.

Moreover, the radiation detector 10 will be described in detail. FIG. 2 is an example of a plan view of the radiation detector 10 according to the present embodiment as seen from the first surface 11A side of the base material 11. Additionally, FIG. 3 is an example of a cross-sectional view taken along line A-A of the radiation detector 10 in FIG. 2.

The base material 11 is a resin sheet that has flexibility and includes, for example, a plastic such as a polyimide (PI). The thickness of the base material 11 may be a thickness such that desired flexibility is obtained depending on the hardness of a material, the size of the sensor substrate 12, that is, the area of the first surface 11A or a second surface 11B, and the like. In a case where a rectangular base material 11 is a single body, an example having flexibility indicates one in which the base material 11 hangs down (becomes lower than the height of the fixed side) 2 mm or more due to the gravity of the base material 11 resulting from its own weight at a position 10 cm away from the fixed side with one side of the base material 11 fixed. As a specific example in a case where the base material 11 is the resin sheet, the thickness thereof may be 5 μm to 125 μm, and the thickness thereof may be more preferably 20 μm to 50 μm.

In addition, the base material 11 has characteristics capable of withstanding the manufacture of the pixels 30 and has characteristics capable of withstanding the manufacture of amorphous silicon TFT (a-Si TFT) in the present embodiment. As such a characteristic of the base material 11, it is preferable that the coefficient of thermal expansion (CTE) at 300° C. to 400° C. is about the same as that of amorphous silicon (a-Si) wafer (for example, ±5 ppm/K), specifically, the coefficient of thermal expansion is preferably 20 ppm/K or less. Additionally, as the thermal shrinkage rate of the base material 11, it is preferable that the thermal shrinkage rate at 400° C. is 0.5% or less with the thickness being 25 μm. Additionally, it is preferable that the elastic modulus of the base material 11 does not have a transition point that general PI has, in a temperature region of 300° C. to 400° C., and the elastic modulus at 500° C. is 1 GPa or more.

Additionally, it is preferable that the base material 11 of the present embodiment has a fine particle layer containing inorganic fine particles having an average particle diameter of 0.05 μm or more and 2.5 μm or less, which absorbs backscattered rays by itself in order to suppress backscattered rays. In addition, as the inorganic fine particles, in the case of the resinous base material 11, it is preferable to use an inorganic substance of which the atomic number is larger than the atoms constituting the organic substance that is the base material 11 and is 30 or less. Specific examples of such fine particles include $SiO_2$ that is an oxide of Si having an atomic number of 14, MgO that is an oxide of Mg having an atomic number of 12, $Al_2O_3$ that is an oxide of Al having an atomic number of 13, $TiO_2$ that is an oxide of Ti having an atomic number of 22, and the like. A specific example of the resin sheet having such characteristics is XENOMAX (registered trademark).

In addition, the above thicknesses in the present embodiment were measured using a micrometer. The coefficient of thermal expansion was measured according to JIS K7197:1991. In addition, the measurement was performed by cutting out test pieces from a main surface of the base material 11 while changing the angle by 15 degrees, measuring the coefficient of thermal expansion of each of the cut-out test pieces, and setting the highest value as the coefficient of thermal expansion of the base material 11. The coefficient of thermal expansion is measured at intervals of 10° C. between −50° C. and 450° C. in a machine direction (MD) and a transverse direction (TD), and (ppm/° C.) is converted to (ppm/K). For the measurement of the coefficient of thermal expansion, the TMA4000S apparatus made by MAC Science Co., Ltd. is used, sample length is 10 mm, sample width is 2 mm, initial load is 34.5 g/mm², temperature rising rate is 5° C./min, and the atmosphere is in argon.

The base material 11 having desired flexibility is not limited to a resinous material such as the resin sheet. For example, the base material 11 may be a glass substrate or the like having a relatively small thickness. As a specific example of a case where the base material 11 is the glass substrate, generally, in a size of about 43 cm on a side, the glass substrate has flexibility as long as the thickness is 0.3 mm or less. Therefore, any desired glass substrate may be used as long as the thickness is 0.3 mm or less.

As shown in FIGS. 2 and 3, the plurality of pixels 30 are provided on the first surface 11A of the base material 11. In the present embodiment, a region on the first surface 11A of the base material 11 where the pixels 30 are provided is the pixel region 35.

Additionally, the conversion layer 14 is provided on the first surface 11A of the base material 11. The conversion layer 14 of the present embodiment covers the pixel region 35. In the present embodiment, a scintillator including CsI (cesium iodide) is used as an example of the conversion layer 14. It is preferable that such a scintillator includes, for example, CsI:Tl (cesium iodide to which thallium is added) or CsI:Na (cesium iodide to which sodium is added) having an emission spectrum of 400 nm to 700 nm at the time of X-ray irradiation. In addition, the emission peak wavelength in a visible light region of CsI:Tl is 565 nm.

In a case where the conversion layer 14 is formed by the vapor-phase deposition method, as shown in FIG. 3, the conversion layer 14 is formed with an inclination such that the thickness thereof gradually decreases toward an outer edge thereof. In the following, a central region 14A of the conversion layer 14 where the thickness in a case where manufacturing errors and measurement errors are neglected can be considered to be substantially constant is referred to as a central part. Additionally, an outer peripheral region of the conversion layer 14 having a thickness of, for example, 90% or less of the average thickness of the central part 14A of the conversion layer 14 is referred to as a peripheral edge part 14B. That is, the conversion layer 14 has an inclined surface that is inclined with respect to the sensor substrate 12 at the peripheral edge part 14B. In addition, in the following, for convenience of description, in a case where "upper" or "lower" are mentioned on the sensor substrate 12, the conversion layer 14 is used as a reference, the side of the conversion layer 14 facing with the sensor substrate 12 is referred to as "lower", and the opposite side is referred to as "upper". For example, the conversion layer 14 is provided on the sensor substrate 12, and the inclined surface of the peripheral edge part 14B of the conversion layer 14 is inclined in a state where the conversion layer 14 gradually expands from the upper side to the lower side.

Additionally, as shown in FIG. 3, a pressure-sensitive adhesive layer 60, a, reflective layer 62, an adhesive layer 64, and a protective layer 66 are provided on the conversion layer 14 of the present embodiment.

The pressure-sensitive adhesive layer 60 covers the entire surface of the conversion layer 14. The pressure-sensitive adhesive layer 60 has a function of fixing the reflective layer 62 to the conversion layer 14. The pressure-sensitive adhesive layer 60 preferably has optical transmittance. As materials of the pressure-sensitive adhesive layer 60, for example, an acrylic pressure sensitive adhesive, a hot-melt pressure sensitive adhesive, and a silicone adhesive can be used. Examples of the acrylic pressure sensitive adhesive include urethane acrylate, acrylic resin acrylate, epoxy acrylate, and the like. Examples of the hot-melt pressure sensitive adhesive include thermoplastics, such as ethylene-vinyl acetate copolymer resin (EVA), ethylene-acrylate copolymer resin (EAA), ethylene-ethyl acrylate copolymer resin (EEA), and ethylene-methyl methacrylate copolymer (EMMA). The thickness of the pressure-sensitive adhesive layer 60 is preferably 2 μm or more and 7 μm or less. By setting the thickness of the pressure-sensitive adhesive layer 60 to 2 μm or more, the effect of fixing the reflective layer 62 on the conversion layer 14 can be sufficiently exhibited. Moreover, the risk of forming an air layer between the conversion layer 14 and the reflective layer 62 can be suppressed. When an air layer is formed between the conversion layer 14 and the reflective layer 62, there is a concern that multiple reflections may be caused in which the light emitted from the conversion layer 14 repeats reflections between the air layer and the conversion layer 14 and between the air layer and the reflective layer 62. Additionally, by setting the thickness of the pressure-sensitive adhesive layer 60 to 7 μm or less, it is possible to suppress a decrease in modulation transfer function (MTF) and detective quantum efficiency (DQE).

The reflective layer 62 covers the entire surface of the pressure-sensitive adhesive layer 60. The reflective layer 62 has a function of reflecting the light converted by the conversion layer 14. The material of the reflective layer 62 is preferably made of a resin material containing a metal or a metal oxide. As the material of the reflective layer 62, for example, white PET (Polyethylene terephthalate), $TiO_2$, $Al_2O_3$, foamed white PET, specular reflective aluminum, and the like can be used. White PET is obtained by adding a white pigment such as $TiO_2$ or barium sulfate to PET, and foamed white PET is white PET having a porous surface. Additionally, as the material of the reflective layer 62, a laminated film of a resin film and a metal film may be used. Examples of the laminated film of the resin film and the metal film include an Alpet (registered trademark) sheet in which aluminum is laminated by causing an aluminum foil to adhere to an insulating sheet (film) such as polyethylene terephthalate. The thickness of the reflective layer 62 is preferably 10 μm or more and 40 μm or less. In this way, by comprising the reflective layer 62 on the conversion layer 14, the light converted by the conversion layer 14 can be efficiently guided to the pixels 30 of the sensor substrate 12.

The adhesive layer 64 covers the entire surface of the reflective layer 62. An end part of the adhesive layer 64 extends to the first surface 11A of the base material 11. That is, the adhesive layer 64 adheres to the base material 11 of the sensor substrate 12 at the end part thereof. The adhesive layer 64 has a function of fixing the reflective layer 62 and the protective layer 66 to the conversion layer 14. As the material of the adhesive layer 64, the same material as the material of the pressure-sensitive adhesive layer 60 can be used, but the adhesive force of the adhesive layer 64 is preferably larger than the adhesive force of the pressure-sensitive adhesive layer 60.

The protective layer 66 is provided in a state where the protective layer covers the entire conversion layer 14 and the end part thereof covers a part of the sensor substrate 12. The protective layer 66 functions as a moisture proof film that prevents moisture from entering the conversion layer 14. As the material of the protective layer 66, for example, organic films containing organic materials such as PET, polyphenylene sulfide (PPS), oriented polypropylene (OPP: biaxially oriented polypropylene film), polyethylene naphthalate (PEN), and PI, and Parylene (registered trademark) can be used. Additionally, as the protective layer 66, a laminated film of a resin film and a metal film may be used. Examples of the laminated film of the resin film and the metal film include ALPET (registered trademark) sheets.

Meanwhile, as shown in FIGS. 2 and 3, a plurality (16 in FIG. 2) of the terminals 113 are provided on an outer edge part of the first surface 11A of the base material 11. An anisotropic conductive film or the like is used as the terminals 113. As shown in FIGS. 2 and 3, the flexible cable 112 is electrically connected to each of the plurality of terminals 113. Specifically, as shown in FIG. 2, the flexible cable 112A is thermocompression-bonded to each of the plurality of (eight in FIG. 2) terminals 113 provided on one side of the base material 11. The flexible cable 112A is a so-called chip on film (COF), and a driving integrated circuit (IC) 210 is mounted on the flexible cable 112A. The driving IC 210 is connected to each of a plurality of signal lines included in the flexible cable 112A. In addition, in the present embodiment, the flexible cable 112A and the flexible cable 112B to be described below are simply referred to as "flexible cable 112" in a case where the cables are collectively referred to without distinction.

The other end of the flexible cable 112A opposite to the one end electrically connected to the terminal 113 of the sensor substrate 12 is electrically connected to the driving substrate 200. As an example, in the present embodiment, the plurality of signal lines included in the flexible cable 112A are thermocompression-bonded to the driving substrate 200 and thereby electrically connect to circuits and elements (not shown) mounted on the driving substrate 200. In addition, the method of electrically connecting the driving substrate 200 and the flexible cable 112A is not limited to the present embodiment. For example, a configuration may be adopted in which the driving substrate 200 and the flexible cable 112A are electrically connected by a connector. Examples of such a connector include a zero insertion force (ZIF) structure connector and a Non-ZIF structure connector.

The driving substrate 200 of the present embodiment is a flexible printed circuit board (PCB), which is a so-called flexible substrate. Additionally, circuit components (not shown) mounted on the driving substrate 200 are components mainly used for processing digital signals (hereinafter, referred to as "digital components"). Digital components tend to have a relatively smaller area (size) than analog components to be described below. Specific examples of the digital components include digital buffers, bypass capacitors, pull-up/pull-down resistors, damping resistors, electromagnetic compatibility (EMC) countermeasure chip components, power source ICs, and the like. In addition, the driving substrate 200 may not be necessarily a flexible substrate and may be a non-flexible rigid substrate or a rigid flexible substrate.

In the present embodiment, the drive unit 102 is realized by the driving substrate 200 and the driving IC 210 mounted on the flexible cable 112A. In addition, the driving IC 210 includes, among various circuits and elements that realize the drive unit 102, circuits different from the digital components mounted on the driving substrate 200.

Meanwhile, the flexible cable 112B is electrically connected to each of the plurality (eight in FIG. 2) of terminals 113 provided on a side intersecting with one side of the base material 11 to which the flexible cable 112A is electrically connected. Similar to the flexible cable 112A, the flexible cable 112B is a so-called chip on film (COF), and a signal processing IC 310 is mounted on the flexible cable 112B. The signal processing IC 310 is connected to a plurality of signal lines (not shown) included in the flexible cable 112B.

The other end of the flexible cable 112B opposite to one end electrically connected to the terminal 113 of the sensor substrate 12 is electrically connected to the signal processing substrate 300. As an example, in the present embodiment, the plurality of signal lines included in the flexible cable 112B are thermocompression-bonded to the signal processing substrate 300 and thereby electrically connected to the circuits and elements (not shown) mounted on the signal processing substrate 300. In addition, the method of electrically connecting the signal processing substrate 300 and the flexible cable 112B is not limited to the present embodiment. For example, a configuration may be adopted in which the signal processing substrate 300 and the cable 112B are electrically connected by a connector. Examples of such a connector include a connector having a ZIF structure, a connector having a Non-ZIF structure, and the like. Additionally, the method of electrically connecting the flexible cable 112A and the driving substrate 200 and the method of electrically connecting the flexible cable 112B and the signal processing substrate 300 may be the same or different. For example, a configuration may be adopted in which the flexible cable 112A and the driving substrate 200 are electrically connected by thermocompression bonding, and the flexible cable 112B and the signal processing substrate 300 are electrically connected by a connector.

The signal processing substrate 300 of the present embodiment is a flexible PCB, which is a so-called flexible substrate, similarly to the above-described driving substrate 200. Circuit components (not shown) mounted on the signal processing substrate 300 are components mainly used for processing analog signals (hereinafter referred to as "analog components"). Specific examples of the analog components include charge amplifiers, analog-to-digital converters (ADCs), digital-to-analog converters (DAC), and power source ICs. Additionally, the circuit components of the present embodiment also include coils around a power source, which has a relatively large component size, and large-capacity smoothing capacitors. In addition, the signal processing substrate 300 may not be necessarily a flexible substrate and may be a non-flexible rigid substrate or a rigid flexible substrate.

In the present embodiment, the signal processing unit 104 is realized by the signal processing substrate 300 and the signal processing IC 310 mounted on the flexible cable 112B. In addition, the signal processing IC 310 includes, among various circuits and elements that realize the signal processing unit 104, circuits different from the analog components mounted on the signal processing substrate 300.

In addition, in FIG. 2, a configuration in which a plurality of (two) the driving substrates 200 and a plurality of (two) the signal processing substrates 300 are provided has been described. However, the number of driving substrates 200 and the number of signal processing substrates 300 are not limited to those shown in FIG. 2. For example, a configuration may be adopted in which at least one of the driving substrate 200 or the signal processing substrate 300 may be a single substrate.

Meanwhile, as shown in FIG. 3, in the radiation detector 10 of the present embodiment, the flexible cable 112 is thermocompression-bonded to the terminal 113, and thereby the flexible cable 112 is electrically connected to the terminal 113. In addition, although FIG. 3 is a view showing an example of a structure relating to the electrical connection between the flexible cable 112B and the radiation detector 10, a structure related to the electrical connection between the flexible cable 112A and the radiation detector 10 of the present embodiment is also the same as the configuration shown in FIG. 3.

Additionally, as shown in FIG. 3, an antistatic layer 48, and an electromagnetic shield layer 44 are provided in order from the one closest to the second surface 11B on the second surface 11B side of the base material 11 in the sensor substrate 12 of the radiation detector 10 of the present embodiment.

The antistatic layer 48 has a function of preventing the sensor substrate 12 from being charged and has a function of suppressing the influence of static electricity. As the antistatic layer 48, for example, an antistatic paint "Colcoat" (product name: made by Colcoat), PET, polypropylene (PP), and the like can be used.

The electromagnetic shield layer 44 has a function of suppressing the influence of electromagnetic wave noise from the outside. As the material of the electromagnetic shield layer 44, for example, a laminated film of a resin film such as Alpet (registered trademark) and a metal film can be used.

Additionally, as shown in FIGS. 2 and 3, a reinforcing substrate 40 including the porous layer 50 is provided on the conversion layer 14, specifically on the protective layer 66, by the pressure sensitive adhesive 42.

The reinforcing substrate 40 has a function of reinforcing the stiffness of the base material 11. The reinforcing substrate 40 of the present embodiment is higher in bending stiffness than the base material 11, and the dimensional change (deformation) thereof with respect to a force applied in a direction perpendicular to the surface facing the conversion layer 14 is smaller than the dimensional change thereof with respect to a force applied in the direction perpendicular to the second surface 11B of the base material 11. In addition, specifically, the bending stiffness of the reinforcing substrate 40 is preferably 100 times or more the bending stiffness of the base material 11. Additionally, the thickness of the reinforcing substrate 40 of the present embodiment is larger than the thickness of the base material 11. For example, in a case where XENOMAX (registered trademark) is used as the base material 11, the thickness of the reinforcing substrate 40 is preferably about 0.1 mm to 0.25 mm.

Specifically, a material having a bending elastic modulus of 150 MPa or more and 2,500 MPa or less is preferably used for the reinforcing substrate 40 of the present embodiment. From the viewpoint of suppressing the deflection of the base material 11, the reinforcing substrate 40 preferably has a higher bending stiffness than the base material 11. In addition, in a case where the bending elastic modulus becomes low, the bending stiffness also becomes low. In order to obtain a desired bending stiffness, the thickness of the reinforcing substrate 40 should be made large, and the thickness of the entire radiation detector 10 increases. Considering the material of the above-described reinforcing substrate 40, the thickness of the reinforcing substrate 40 tends to be relatively large in a case where a bending stiffness exceeding 140,000 Pacm⁴ is to be obtained. For that reason, in view of obtaining appropriate stiffness and considering the thickness of the entire radiation detector 10, the material used for the reinforcing substrate 40 preferably has a bending elastic modulus of 150 MPa or more and 2,500 MPa or less. Additionally, the bending stiffness of the reinforcing substrate 40 is preferably 540 Pacm⁴ or more and 140,000 Pacm⁴ or less.

Additionally, the coefficient of thermal expansion of the reinforcing substrate 40 of the present embodiment is preferably closer to the coefficient of thermal expansion of the material of the conversion layer 14, and the ratio of the coefficient of thermal expansion of the reinforcing substrate 40 to the coefficient of thermal expansion of the conversion layer 14 (the coefficient of thermal expansion of the reinforcing substrate 40/the coefficient of thermal expansion of the conversion layer 14) is more preferably 0.5 or more and 2 or less. The coefficient of thermal expansion of such a reinforcing substrate 40 is preferably 30 ppm/K or more and 80 ppm/K or less. For example, in a case where the conversion layer 14 has CsI:Tl as a material, the coefficient of thermal expansion is 50 ppm/K. In this case, examples of materials relatively close to the conversion layer 14 include polyvinyl chloride (PVC) having a coefficient of thermal expansion of 60 ppm/K to 80 ppm/K, PET having a coefficient of thermal expansion of 65 ppm/K to 70 ppm/K, polycarbonate (PC) having a coefficient of thermal expansion of 65 ppm/K, and the like.

From the viewpoint of elasticity, the reinforcing substrate 40 more preferably contains a material having a yield point. In addition, in the present embodiment, the "yield point" means a phenomenon in which the stress rapidly decreases once in a case where the material is pulled, means that the strain is increased without increasing the stress on a curve representing a relationship between the stress and the strain, and indicates the peak of a stress-strain curve in a case where a tensile strength test is performed on the material. Resins having the yield point generally include resins that are hard and strongly sticky, and resins that are soft and strongly sticky and have medium strength. Examples of the hard and strongly sticky resins include PC and the like. Additionally, examples of the resins that are soft and strongly sticky and have medium strength include PP and the like.

Figure 4A:
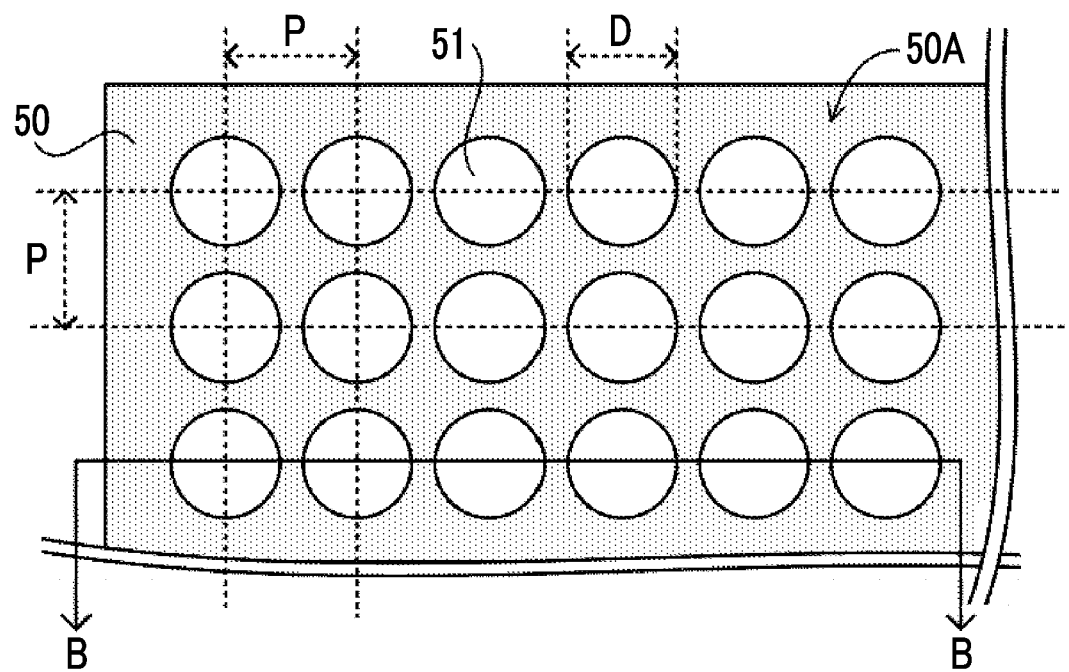
FIG. 4A is a plan view of an example of a porous layer having a punching structure as seen from an upper surface side of the radiation detector.

Additionally, as described above, the reinforcing substrate 40 of the present embodiment includes the porous layer 50. FIG. 4A is a plan view of an example of the porous layer 50 of the present embodiment as seen from the upper surface side of the radiation detector 10. Additionally, FIG. 4B is an example of a cross-sectional view taken along line B-B of the porous layer 50 in FIG. 4A.

Figure 4B:
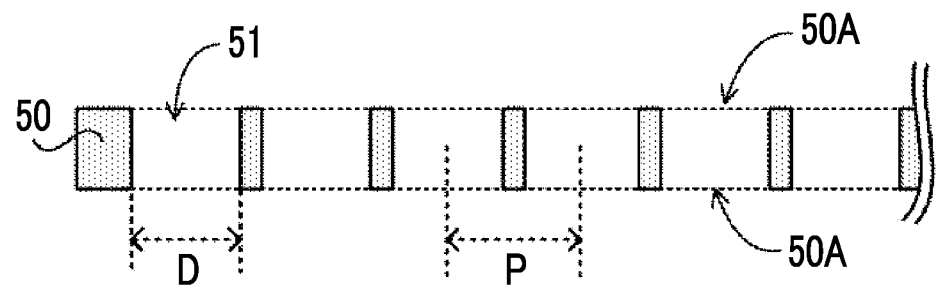
FIG. 4B is an example of a cross-sectional view taken along line B-B of the porous layer shown in FIG. 4A.

As shown in FIGS. 4A and 4B, the porous layer 50 has a plurality of through-holes 51. The porous layer 50 shown in FIGS. 4A and 4B has a circular opening portion and has a so-called punching structure in which a plurality of through-holes 51 penetrating from an upper surface 50A to a lower surface 50B are arranged in parallel. By having the plurality of through-holes 51 in this way, the weight of the reinforcing substrate 40 is reduced.

In addition, the opening diameter D, pitch P, and opening ratio of the through-holes 51 of the porous layer 50 influence the bending stiffness of the reinforcing substrate 40. For example, as the opening ratio of the through-hole 51 increases, the bending stiffness of the reinforcing substrate 40 tends to decrease. In addition, the opening ratio refers to the ratio of opening portions of the through-holes 51 to the total area, and the smaller the pitch P with respect to the opening diameter D, the higher the opening ratio. For example, in the case of the porous layer 50 shown in FIG. 4A, the opening ratio is calculated by the following Equation (1).

$$\text{Opening ratio (\%)} = (78.5 \times D^2)/P^2 \quad (1)$$

For that reason, in order to reduce the weight of the reinforcing substrate 40 and obtain the above-described desired bending stiffness, the pitch P of the through-holes 51 is 1 mm or more and 50 mm or less, the opening diameter D is 0.5 mm or more and 50 mm or less, and the opening ratio is preferably 10% or more and 50% or less.

Figure 5A:
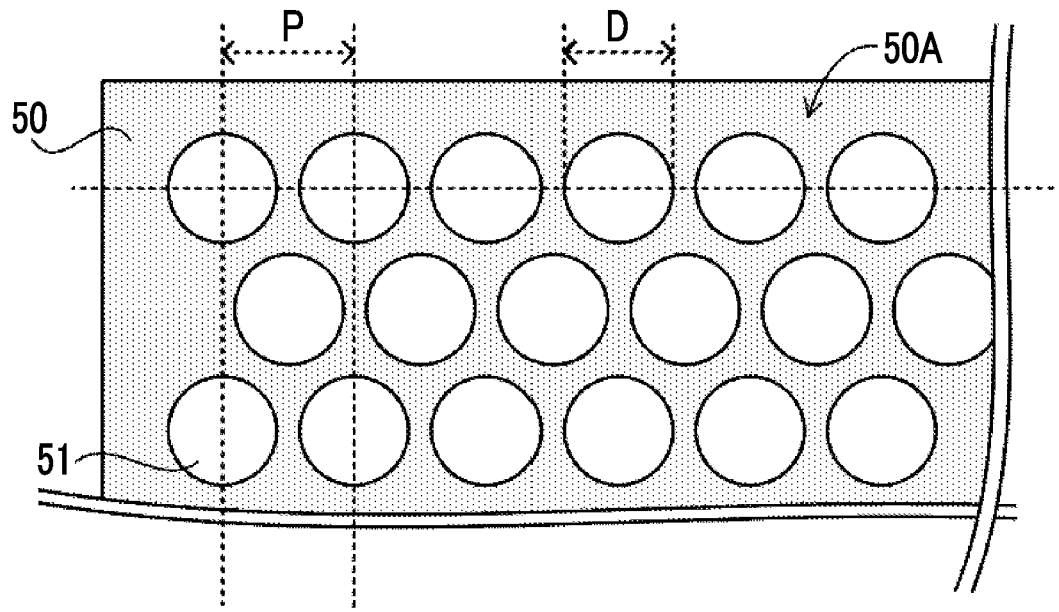
FIG. 5A is a plan view of another example of the porous layer having the punching structure as seen from the upper surface side of the radiation detector.
Figure 5B:
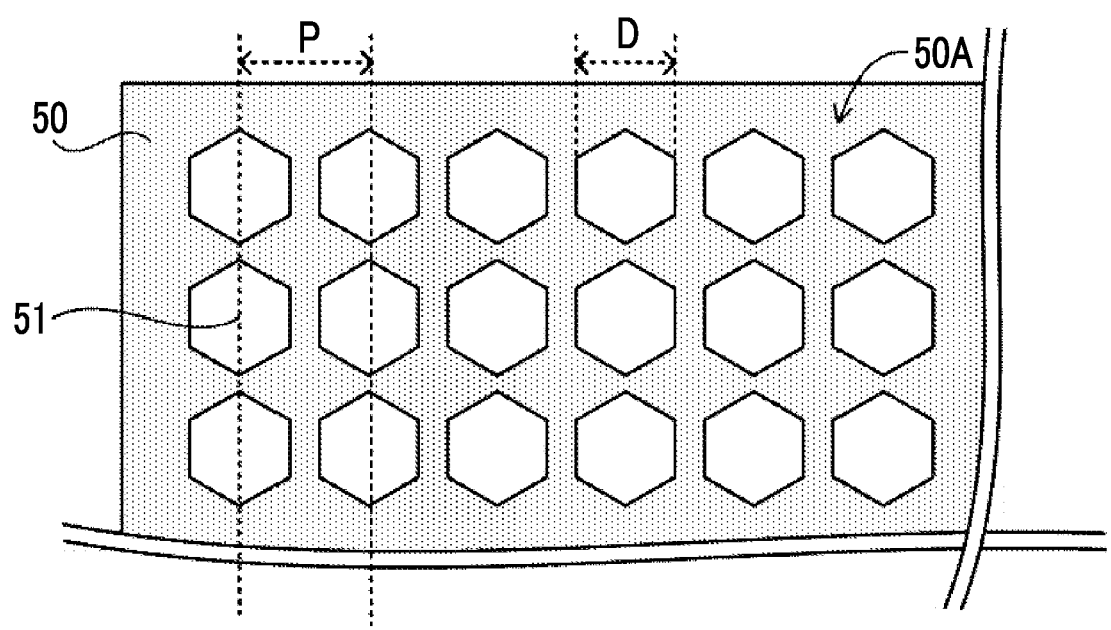
FIG. 5B is a plan view of another example of the porous layer having the punching structure as seen from the upper surface side of the radiation detector.

In addition, the shape of the through-holes 51, for example, the shape and arrangement of the opening portions of the through-holes 51, are not limited to the configuration shown in FIGS. 4A and 4B. For example, as shown in FIG. 5A, the through-holes 51 may be disposed alternately. The example shown in FIG. 5A shows a configuration in which the through-holes 51 are disposed in each row with a half pitch shifted. Additionally, for example, as shown in FIG. 5B, the shape of the opening portions of the through-holes 51 may be a hexagonal shape.

Additionally, the porous layer 50 may have a plurality of through-holes 51, and is not limited to those having the punching structure. Additionally, the through-holes 51 may penetrate at least a part of the porous layer 50, and is not limited to, for example, penetrating the upper surface 50A and the lower surface 50B.

Figure 6A:
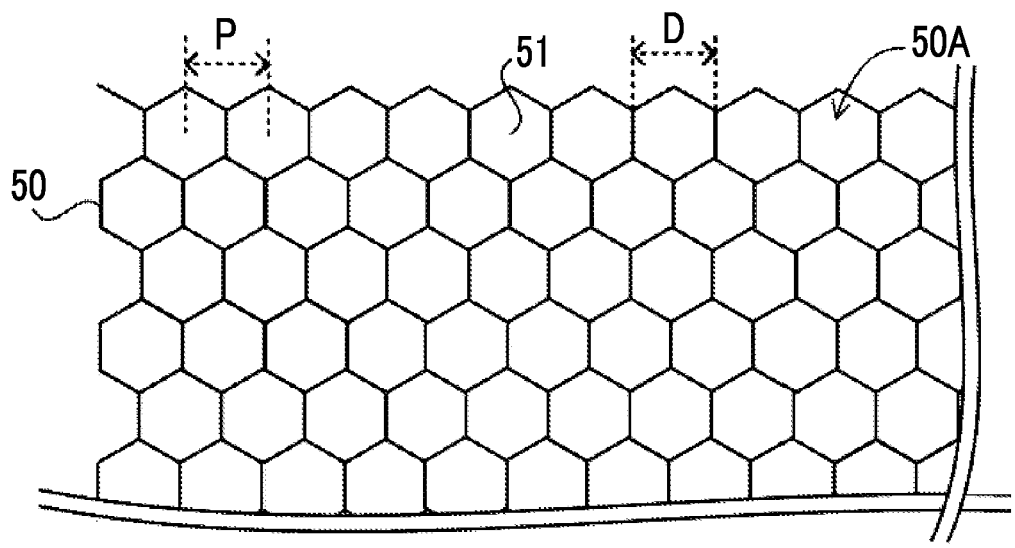
FIG. 6A is a plan view of an example of the porous layer having a honeycomb structure as seen from the upper surface side of the radiation detector.
Figure 6B:
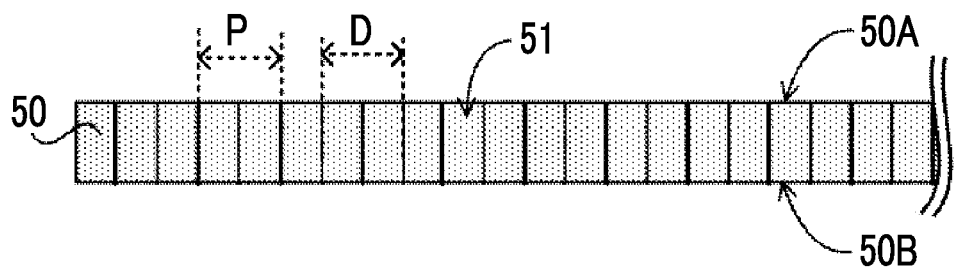
FIG. 6B is a side view of the porous layer shown in FIG. 6A as seen from a side surface side of the radiation detector.

As another example of the porous layer 50, FIGS. 6A and 6B show an example of the porous layer 50 having a honeycomb structure. FIG. 6A is a plan view of an example of the porous layer 50 having a honeycomb structure as seen from the upper surface side of the radiation detector 10. Additionally, FIG. 6B is an example of a side view of the porous layer 50 shown in FIG. 6A as seen from a side surface side of the radiation detector 10.

The porous layer 50 shown in FIGS. 6A and 6B has a plurality of hexagonal through-holes 51 forming a honeycomb structure. In addition, even in the porous layer 50 having a honeycomb structure, the opening diameter D and the pitch P of the through-holes 51 influence the bending stiffness of the reinforcing substrate 40. Therefore, the values of the opening diameter D and the pitch P of the through-hole 51 are preferably within the above-described ranges.

Figure 6C:
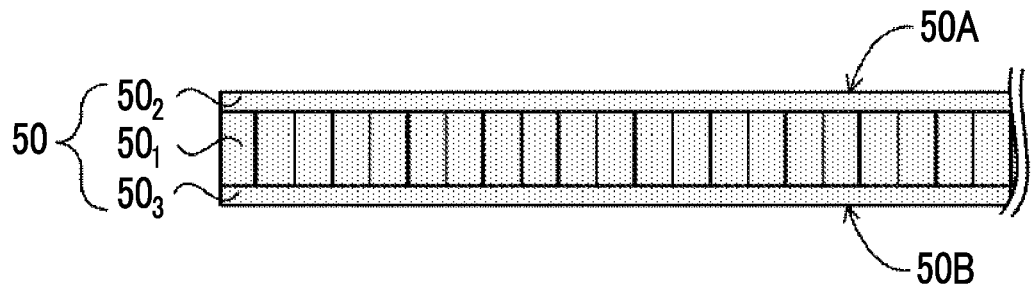
FIG. 6C is a side view of another example of the porous layer having the honeycomb structure as seen from the side surface side of the radiation detector.

In addition, in the case of the porous layer 50 having a honeycomb structure, as in the example shown in FIG. 6C, the honeycomb structure may be a sandwich structure in which a porous plate $50_1$ having a honeycomb structure is sandwiched between a protective plate $50_2$ and a protective plate $50_3$ having no through-hole 51. Additionally, the porous layer 50 may be a laminate of any one of the protective plate $50_2$ and the protective plate $50_3$ and the porous plate $50_1$. In this way, by having at least one of the protective plate $50_2$ and the protective plate $50_3$, the surface area serving as an adhesive surface becomes large. Therefore, for example, the porous layer 50 can be easily bonded to an upper surface of the conversion layer 14. Additionally, the porous layer 50 is firmly fixed to the conversion layer 14.

Figure 7A:
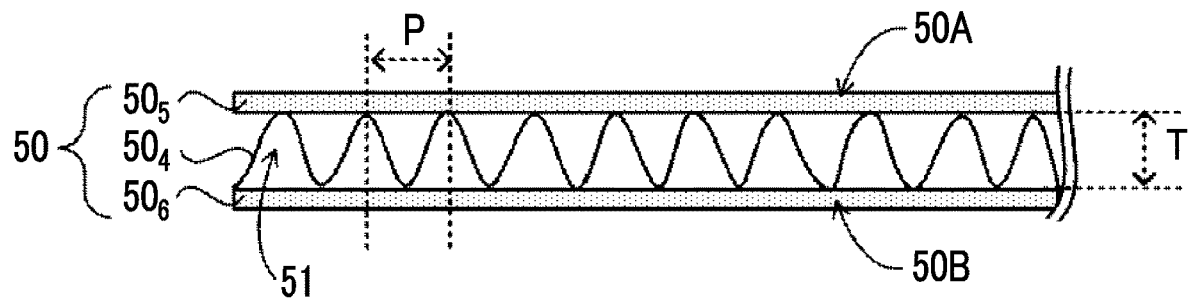
FIG. 7A is a side view of an example of the porous layer having a flute structure as seen from the side surface side of the radiation detector.

Additionally, FIG. 7A shows an example of a side view of the porous layer 50 having a flute structure as seen from the side surface side of the radiation detector 10. The porous layer 50 shown in FIG. 7A has a flute structure in which a corrugated core $50_4$ may be sandwiched between a protective plate $50_5$ and a protective plate $50_6$ corresponding to so-called liners. In addition, the porous layer 50 having a flute structure is not limited to the configuration shown in FIG. 7A, and may have at least one of the protective plate $50_5$ and the protective plate $50_6$.

In the porous layer 50 shown in FIG. 7A, an extension direction of the flute by the core $50_4$ is an in-plane direction of the reinforcing substrate 40. In the case of the porous layer 50 having a flute structure in this way, a plurality of through-holes 51 penetrating from a side surface of the porous layer 50 to the opposite side surface are formed by the core $50_4$.

In the case of the porous layer 50 having a flute structure, the pitch P and the thickness T influence the bending stiffness of the reinforcing substrate 40. For example, the larger the pitch as compared to the thickness T, the lower the bending stiffness tends to be. For that reason, in order to reduce the weight of the reinforcing substrate 40 and obtain the above-described desired bending stiffness, the pitch P of the flute structure is preferably the thickness T or more and three times or less the thickness T. Additionally, the thickness T is preferably 2 mm or less.

Figure 8:
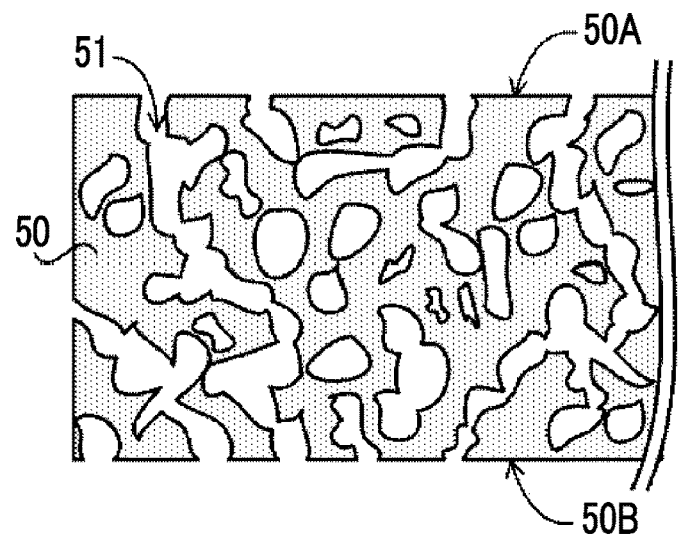
FIG. 8 is a side view of an example of the porous layer having a porous structure as seen from the side surface side of the radiation detector.

Additionally, FIG. 8 shows an example of a side view of the porous layer 50 having a porous structure as seen from the side surface side of the radiation detector 10. In the case of the porous layer 50 having a porous structure, the porosity according to the JIS H7009 standard, particularly the porosity and the pore diameter of through-pores, which are the through-holes 51 influence the bending stiffness of the reinforcing substrate 40. For example, the larger the porosity, the lower the bending stiffness tends to be. In addition, the porosity is the ratio of the volume of the pores to the bulk volume, which is the volume of a porous structure including all pores without being limited to the through-pores, and the through-pore porosity is the ratio of the volume of the through-pores to the bulk volume. Additionally, the pore diameter is the diameter of the pores, and in the case of anisotropic pores, the pore diameter is the diameter of the pores in a cross section of which a major axis direction is vertical. For that reason, in order to reduce the weight of the reinforcing substrate 40 and obtain the above-described desired bending stiffness, the porosity of the porous structure is preferably 15% or more and 50% or less, and the pore diameter is preferably 0.3 μm or more and 5 mm or less.

Examples of resin as the material of the porous layer 50 as described above include at least one of carbon fiber reinforced plastics (CFRP), carbon fiber reinforced thermo plastics (CFRTP), PVC, PET, PP, or PE. Additionally, examples of metal as the material of the porous layer 50 include at least one of aluminum and magnesium. In addition, CFRP of these materials is more preferable for the porous layer 50. In particular, the protective plates $50_2$ and $50_3$ in the porous layer 50 of the honeycomb structure shown in FIG. 6C, and the protective plates $50_5$ and $50_6$ in the flute structure shown in FIG. 7A, respectively, are preferable by using a combination of two layers of CFRP having different stretching directions of the carbon fibers because the bending stiffness can be further improved.

In addition, the reinforcing substrate 40 may include a laminated body in which a plurality of porous layers 50 are laminated. For example, the reinforcing substrate 40 may include a laminated body in which a resinous porous layer 50 and a metallic porous layer 50 are laminated. In this case, the reinforcing substrate 40 can suppress the charges caused by the resinous porous layer 50 with the metallic porous layer 50. Additionally, for example, the reinforcing substrate 40 may include a laminated body in which a plurality of porous layers 50 are laminated, in which the positions of the through-holes 51 are different. In this case, the reinforcing substrate 40 can improve the thermal conductivity by shifting the positions of the through-holes 51, more specifically, the openings in each of the porous layers 50.

Figure 7B:
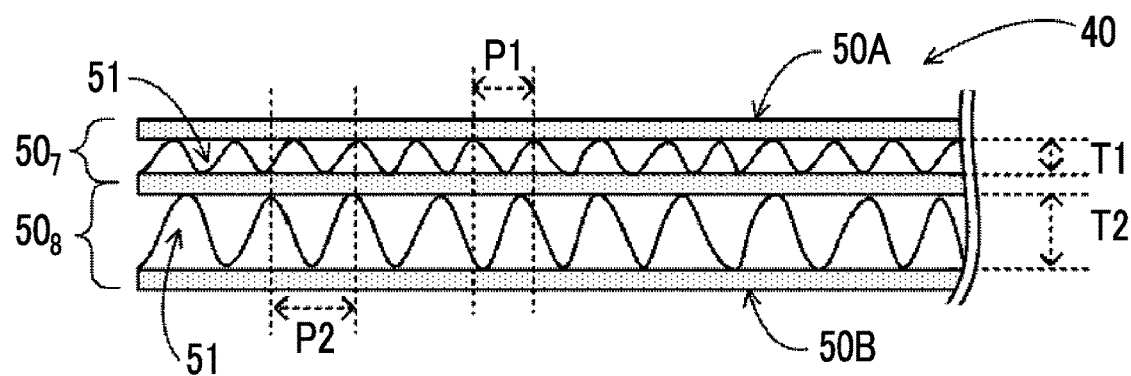
FIG. 7B is a side view of another example of the porous layer having the flute structure as seen from the side surface side of the radiation detector.

Additionally, for example, the reinforcing substrate 40 may include a laminated body in which two porous layers 50 having different pitches P and thicknesses T of the flute structure are laminated. FIG. 7B shows an example of the porous layer 50 having a flute structure in this case, which is an example of a side view as seen from the side surface side of the radiation detector 10. The reinforcing substrate 40 shown in FIG. 7B includes a laminated body in which a porous layer $50_7$ having a flute structure having a pitch P1 and a thickness T1 and a porous layer $50_8$ having a flute structure having a pitch P2 and a thickness T2 are laminated. In this case, the reinforcing substrate 40 can have higher bending stiffness.

Figure 9A:
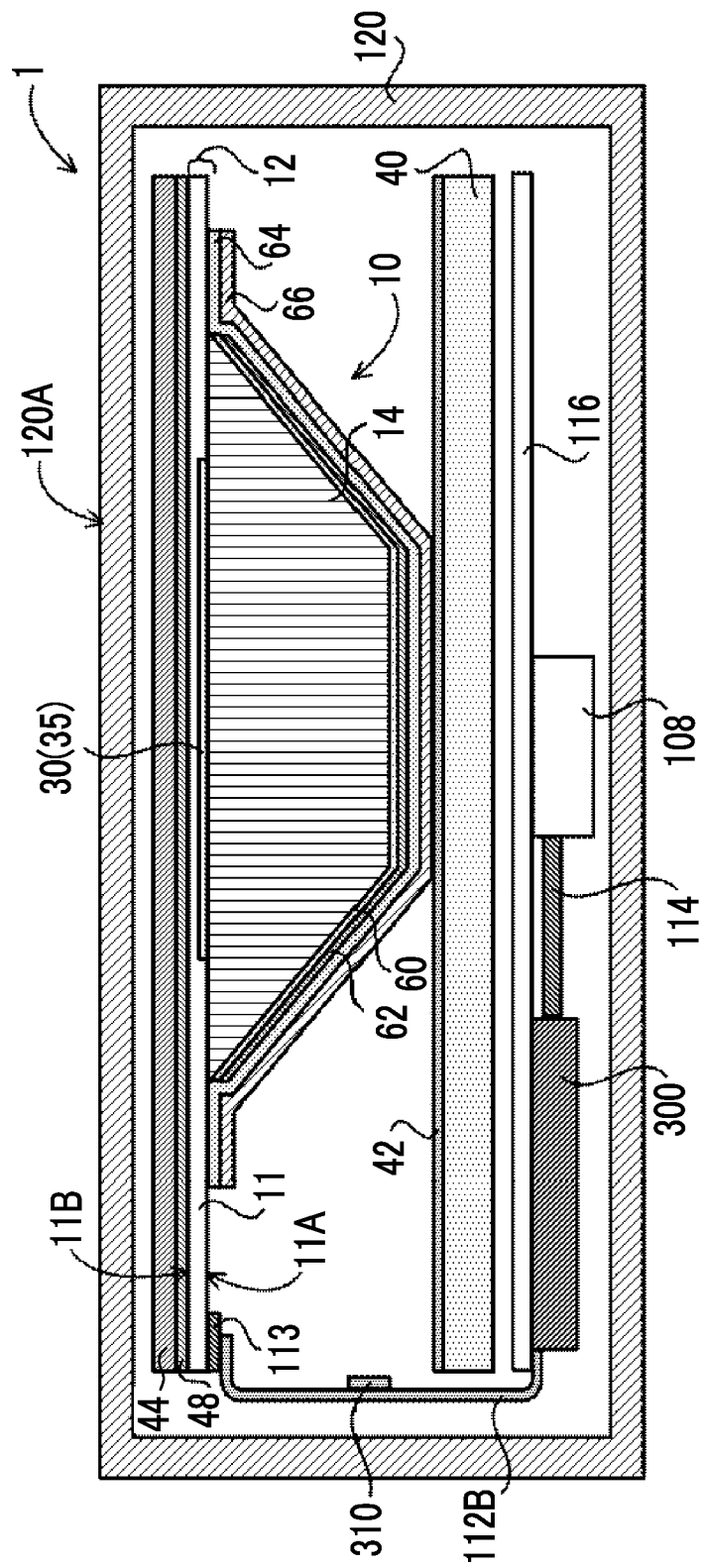
FIG. 9A is a cross-sectional view of an example of the radiographic imaging apparatus according to the embodiment.

Moreover, the radiographic imaging apparatus 1 will be described in detail. FIG. 9A is an example of a cross-sectional view of a radiographic imaging apparatus 1 in a case where the radiation detector 10 of the present embodiment is applied to an irradiation side sampling (ISS) type in which radiation is irradiated from the second surface 11B side of the base material 11. Additionally, FIG. 9B is an example of a cross-sectional view of the radiographic imaging apparatus 1 in a case where the radiation detector 10 of the present embodiment is applied to the penetration side sampling (PSS) type in which radiation is emitted from the conversion layer 14 side.

Figure 9B:
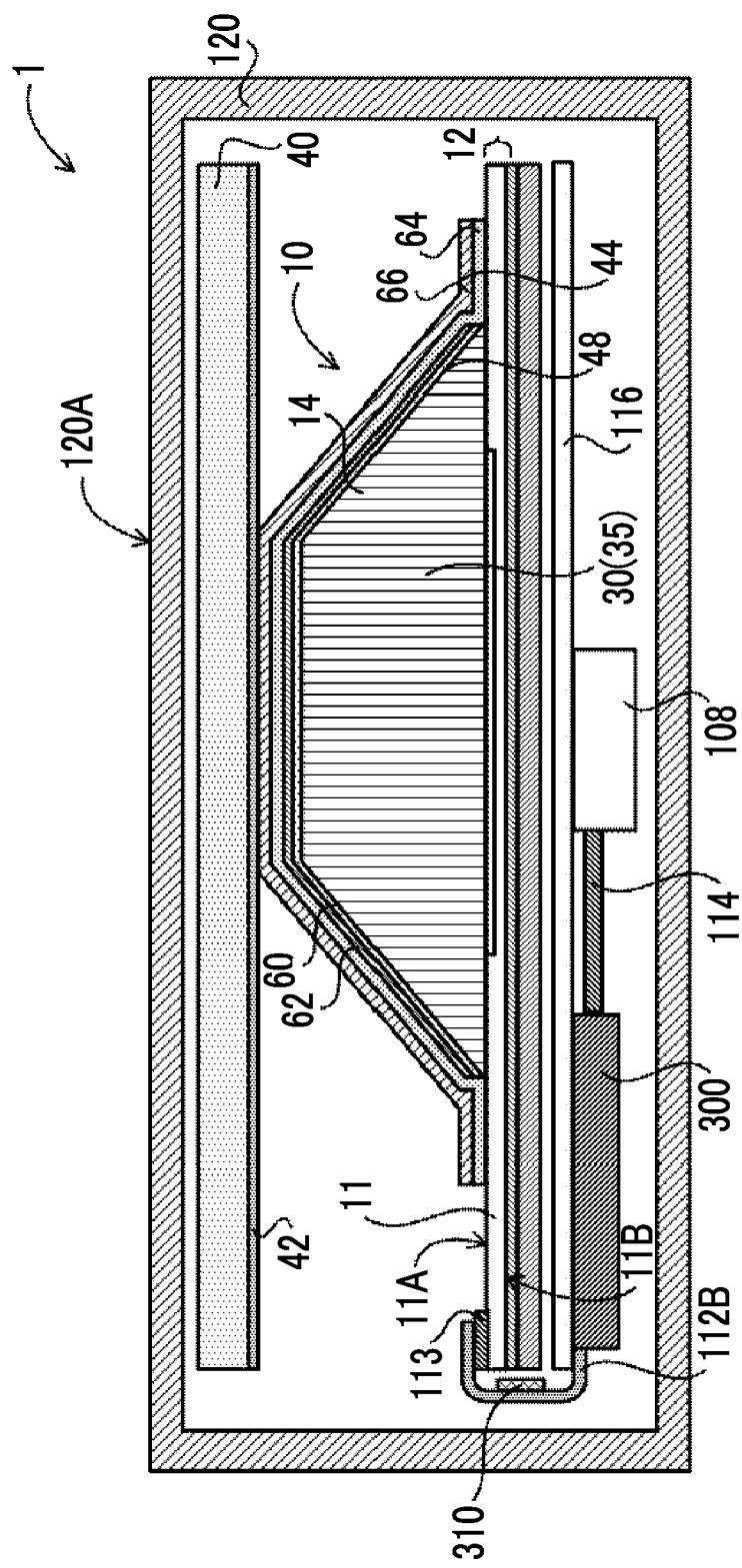
FIG. 9B is a cross-sectional view of an example of the radiographic imaging apparatus according to the embodiment.

The radiographic imaging apparatus 1 formed of the above radiation detector 10 is used while being housed in a housing 120, as shown in FIGS. 9A and 9B. As shown in FIGS. 9A and 9B, the radiation detector 10, the power source unit 108, and the circuit unit such as the signal processing substrate 300 are provided side by side in an incidence direction of radiation within the housing 120. The radiation detector 10 of FIG. 9A is disposed in a state where the second surface 11B of the base material 11 faces a top plate on an irradiation surface 120A side of the housing 120 that is irradiated with the radiation transmitted through a subject. More specifically, the reinforcing substrate 40 is disposed so as to face the top plate on the irradiation surface 120A side of the housing 120. Additionally, the radiation detector 10 of FIG. 9B is disposed in a state where the first surface 11A side of the base material 11 faces the top plate on the irradiation surface 120A side of the housing 120. More specifically, an upper surface of the conversion layer 14 is disposed so as to face the top plate on the irradiation surface 120A side of the housing 120.

Additionally, a middle plate 116 is further provided on a side from which the radiation transmitted through the radiation detector 10 is emitted, within the housing 120 as shown in FIGS. 9A and 9B. The middle plate 116 is, for example, an aluminum or copper sheet. The copper sheet does not easily generate secondary radiation due to incident radiation, and therefore, has a function of preventing scattering to the rear side, that is, the conversion layer 14 side. In addition, it is preferable that the middle plate 116 covers at least an entire surface of the conversion layer 14 from which radiation is emitted, and covers the entire conversion layer 14. Additionally, the circuit unit such as a signal processing substrate 300 is fixed to the middle plate 116.

The housing 120 is preferably lightweight, has a low absorbance of radiation, particularly X-rays, and has a high stiffness, and is more preferably made of a material having a sufficiently high elastic modulus. As the material of the housing 120, it is preferable to use a material having a bending modulus of elasticity of 10,000 MPa or more. As the material of the housing 120, carbon or CFRP having a bending modulus of elasticity of about 20,000 MPa to 60,000 MPa can be suitably used.

In the capturing of a radiographic image by the radiographic imaging apparatus 1, a load from a subject is applied to the irradiation surface 120A of the housing 120. In a case where the stiffness of the housing 120 is insufficient, there are concerns that problems may occur such that the sensor substrate 12 is deflected due to the load from the subject and the pixels 30 are damaged. By housing the radiation detector 10 inside the housing 120 made of a material having a bending modulus of elasticity of 10,000 MPa or more, it is possible to suppress the deflection of the sensor substrate 12 due to the load from the subject.

In addition, the housing 120 may be formed of different materials for the irradiation surface 120A of the housing 120 and other portions. For example, a portion corresponding to the irradiation surface 120A may be formed of a material having a low radiation absorbance and high stiffness and having a sufficiently high elastic modulus, and the other portions may be formed of a material different from the portion corresponding to the irradiation surface 120A, for example, a material having a lower elastic modulus than the portion of the irradiation surface 120A.

In addition, since a porous layer 50 of the present embodiment has a plurality of through-holes 51, the amount of radiation transmitted differs between the portions of the through-holes 51 and portions other than the through-holes 51. Accordingly, there is a case where the amount of radiation that reaches the conversion layer 14 differs. In this case, there is a concern that image unevenness may occur in a radiographic image obtained by the radiation detector 10. For that reason, the radiation detector 10 of the present embodiment is preferably applied to the ISS type radiographic imaging apparatus 1.

A method of manufacturing the radiographic imaging apparatus 1 of the present embodiment will be described with reference to FIGS. 10A to 10F. In addition, the method of manufacturing the radiographic imaging apparatus 1 of the present embodiment includes a method of manufacturing the radiation detector 10 of the present embodiment.

As shown in FIG. 10A, the base material 11 is provided on a support body 400, such as a glass substrate having a thickness larger than that of the base material 11, via a peeling layer 402, for example in order to form the sensor substrate 12. For example, in a case where the base material 11 is formed by a lamination method, a sheet to be the base material 11 is bonded onto the support body 400. The second surface 11B of the base material 11 is in contact with the peeling layer 402. In addition, the method of forming the base material 11 is not limited to the present embodiment. For example, a configuration may be adopted in which the base material 11 is formed by a coating method.

Moreover, the pixels 30 and terminal 113 are formed on the first surface 11A of the base material 11. The pixel 30 is formed via an undercoat layer (not shown) formed of SiN or the like in the pixel region 35 of the first surface 11A. Additionally, a plurality of the terminals 113 are formed along each of two sides of the base material 11.

Figure 10B:
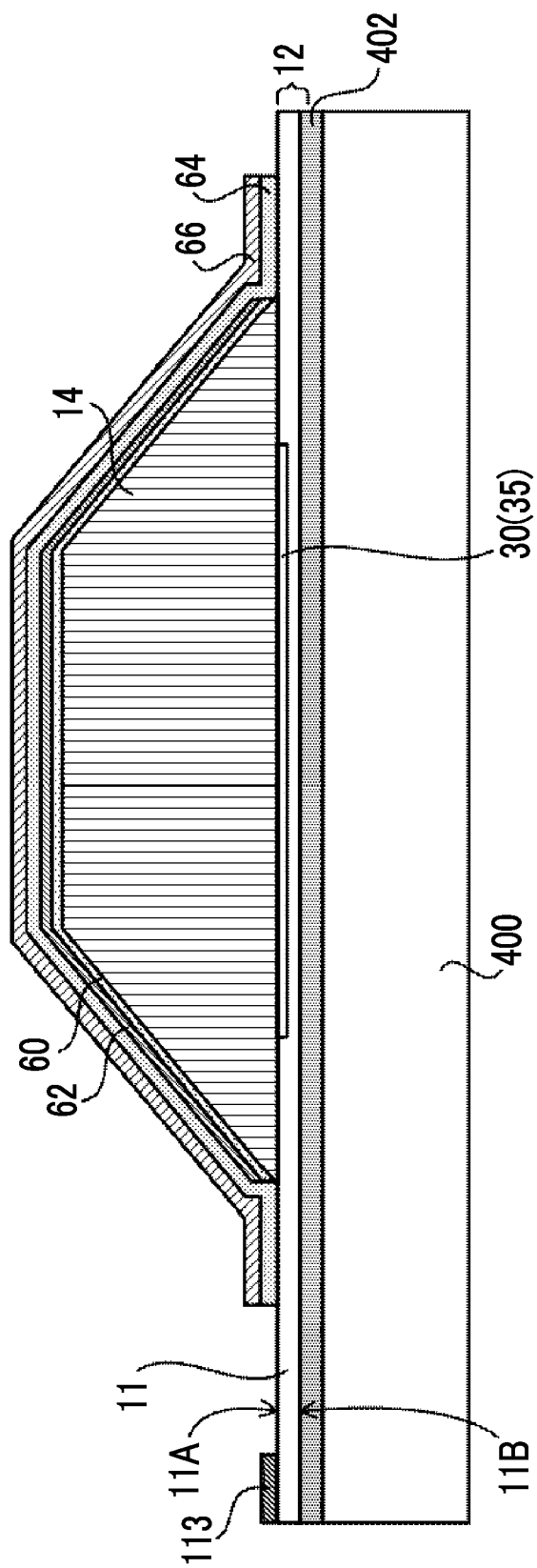
FIG. 10B is a view for explaining an example of the method of manufacturing the radiographic imaging apparatus of the embodiment.

Additionally, as shown in FIG. 10B, the conversion layer 14 is formed on a layer on which the pixels 30 are formed (hereinafter, simply referred to as "pixels 30"). In the present embodiment, the conversion layer 14 of CsI is directly formed as a columnar crystal on the sensor substrate 12 by vapor-phase deposition methods, such as a vacuum vapor deposition method, a sputtering method, and a chemical vapor deposition (CVD) method. In this case, the side of the conversion layer 14 in contact with the pixels 30 is a growth-direction base point side of the columnar crystal.

In addition, in a case where a CsI scintillator is used as the conversion layer 14, the conversion layer 14 can be formed on the sensor substrate 12 by a method different from the method of the present embodiment. For example, the conversion layer 14 may be formed on the sensor substrate 12 by preparing one in which CsI is vapor-deposited on an aluminum or carbon substrate or the like by a vapor-phase deposition method and bonding a side of the CsI, which is not in contact with the substrate, and the pixels 30 of the sensor substrate 12 to each other with a pressure sensitive adhesive sheet or the like. In this case, it is preferable that one in which the entire conversion layer 14 also including a substrate of aluminum or the like is covered with a protective layer is bonded to the pixels 30 of the sensor substrate 12. In addition, in this case, the side of the pixels 30 in contact with the conversion layer 14 is a distal end side in the growth direction of the columnar crystal.

Additionally, unlike the radiation detector 10 of the present embodiment, GOS ($Gd_2O_2S$:Tb)) or the like may be used as the conversion layer 14 instead of CsI. In this case, for example, the conversion layer 14 can be formed on the sensor substrate 12 by preparing one in which a sheet having GOS dispersed in a binder such as resin is bonded to a support body formed of white PET or the like with a pressure-sensitive adhesive layer or the like, and bonding a side of the GOS on which the support body is not bonded, and the pixel 30 of the sensor substrate 12 to each other with the pressure sensitive adhesive sheet or the like. In addition, the conversion efficiency from radiation to visible light is higher in a case where CsI is used for the conversion layer 14 than in a case where GOS is used.

Moreover, the reflective layer 62 is provided on the conversion layer 14 formed on the sensor substrate 12 via the pressure-sensitive adhesive layer 60. Moreover, the protective layer 66 is provided via the adhesive layer 64.

Figure 10C:
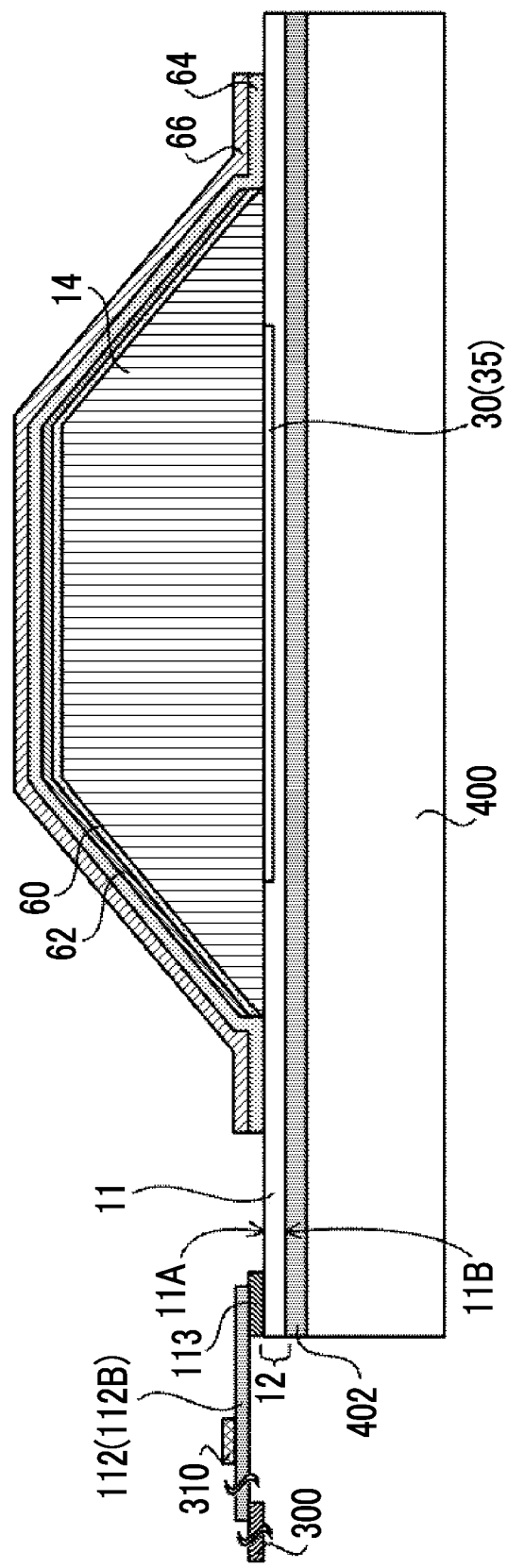
FIG. 10C is a view for explaining an example of the method of manufacturing the radiographic imaging apparatus of the embodiment.

Next, as shown in FIG. 10C, the flexible cable 112 is electrically connected to the sensor substrate 12. Specifically, the flexible cable 112 on which the driving IC 210 or the signal processing IC 310 is mounted is thermocompression-bonded to the terminal 113 to electrically connect the terminal 113 and the flexible cable 112. Accordingly, the flexible cable 112 is electrically connected to the sensor substrate 12.

Figure 10D:
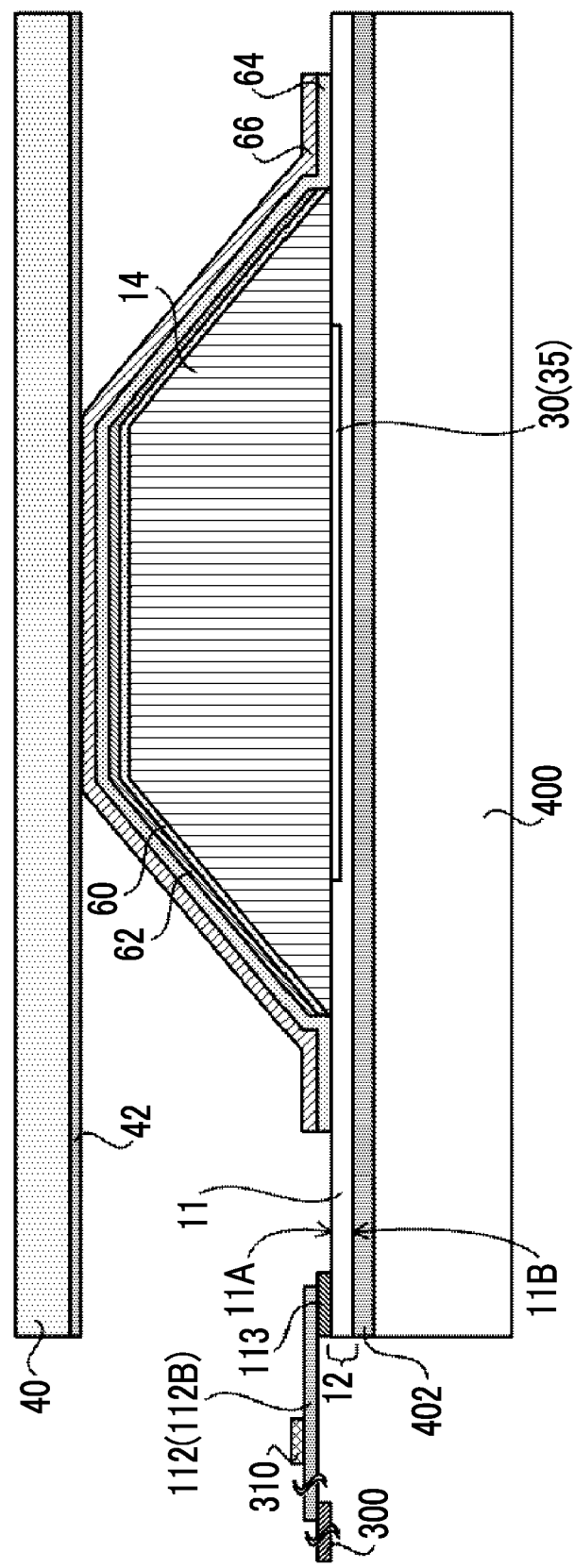
FIG. 10D is a view for explaining an example of the method of manufacturing the radiographic imaging apparatus of the embodiment.

Next, as shown in FIG. 10D, the reinforcing substrate 40 is provided on the conversion layer 14. Specifically, the reinforcing substrate 40 provided with the pressure sensitive adhesive 42 is bonded onto the conversion layer 14 covered with the protective layer 66.

Figure 10E:
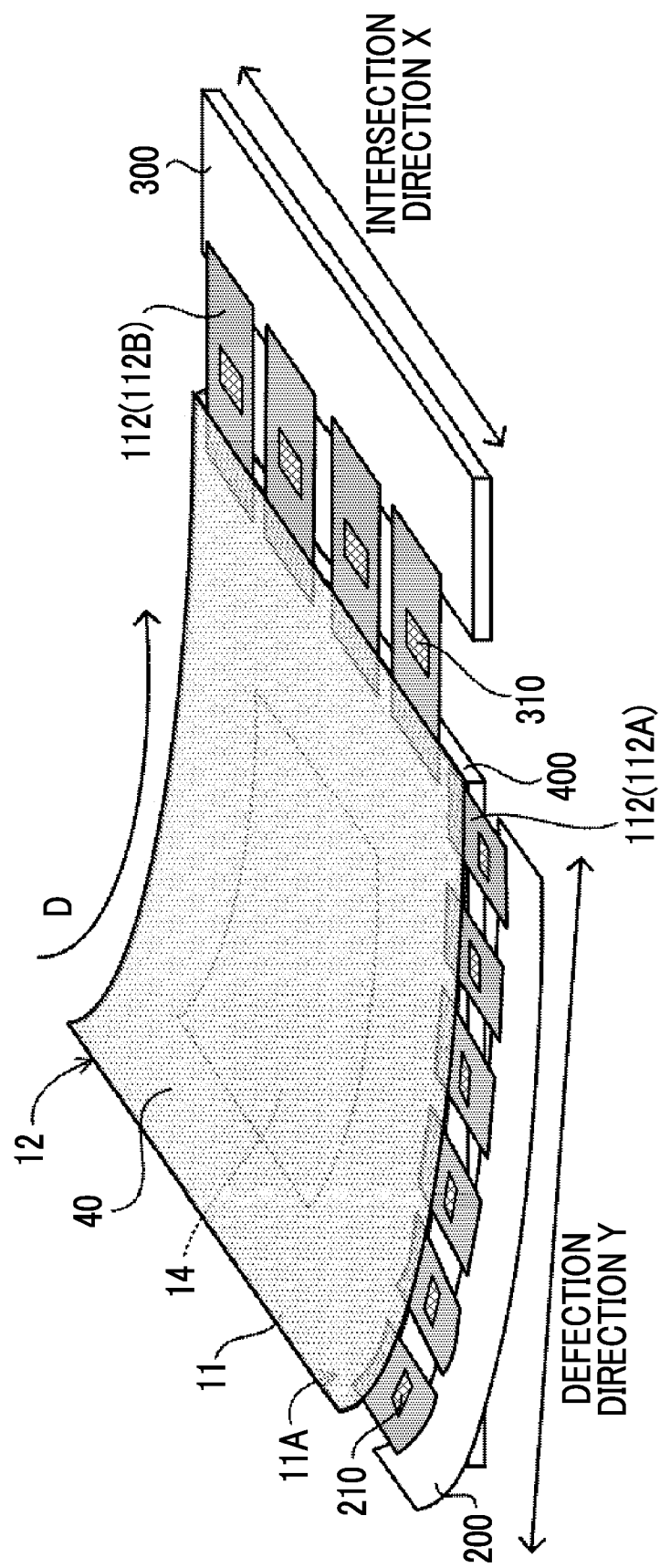
FIG. 10E is a view for explaining an example of the method of manufacturing the radiographic imaging apparatus of the embodiment.

After that, as shown in FIG. 10E, the sensor substrate 12 provided with the conversion layer 14 is peeled from the support body 400. Hereinafter, this step is referred to as a peeling step. In the case of mechanical peeling, in an example shown in FIG. 10E, the side of the base material 11 of the sensor substrate 12 facing the side to which the flexible cable 112B is electrically connected is set as the starting point of the peeling. Also, the sensor substrate 12 is peeled from the support body 400 by gradually pulling off the support body 400 in the direction of an arrow D shown in FIG. 10E from the side to be the starting point toward the side to which the flexible cable 112 is electrically connected.

In addition, it is preferable that the side to be the peeling starting point is a side that intersects the longest side in a case where the sensor substrate 12 is seen in a plan view. In other words, the side in a deflection direction Y in which the deflection is caused by the peeling is preferably the longest side. As an example, in the present embodiment, the peeling starting point is the side opposite to the side to which the flexible cable 112B is electrically connected.

Figure 10F:
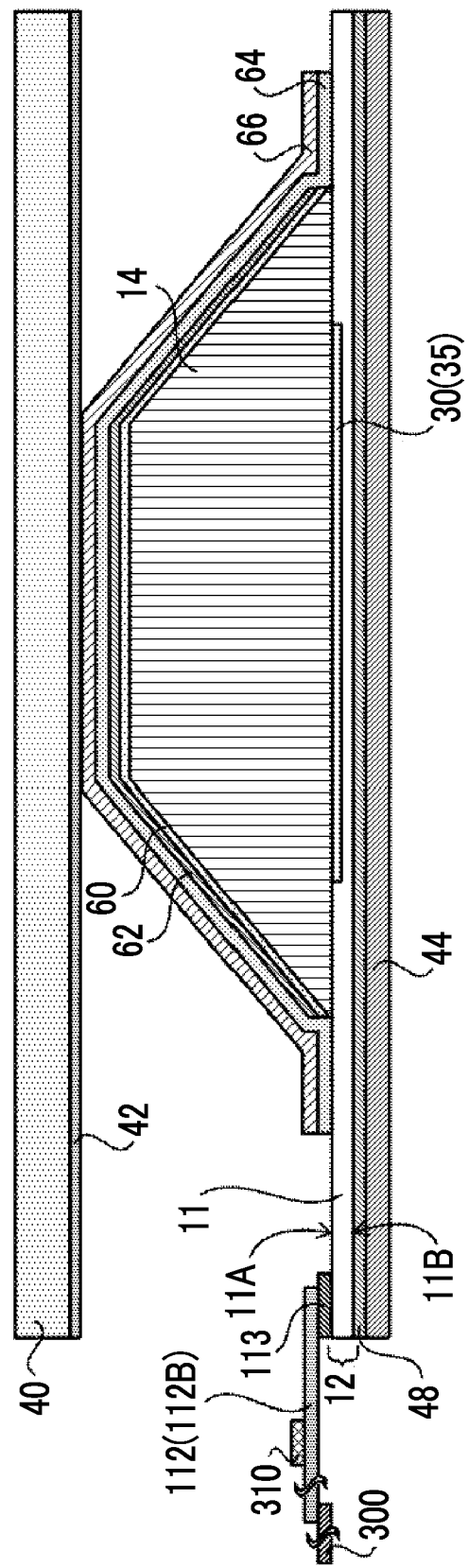
FIG. 10F is a view for explaining an example of the method of manufacturing the radiographic imaging apparatus of the embodiment.

Next, as shown in FIG. 10F, the antistatic layer 48, the electromagnetic shield layer 44, and the reinforcing substrate 40 are sequentially provided on the second surface 11B of the base material 11. Specifically, the antistatic layer 48 and the electromagnetic shield layer 44 are formed on the second surface 11B of the base material 11 by coating or the like.

Moreover, by housing the radiation detector 10, the circuit unit, and the like in the housing 120, the radiographic imaging apparatus 1 shown in FIG. 9A or FIG. 9B is manufactured. Specifically, by housing the radiation detector 10 in the housing 120 in a state where the second surface 11B side of the base material 11, specifically, an electromagnetic shield layer 44 faces the irradiation surface 120A, the radiographic imaging apparatus 1 shown in FIG. 9A is manufactured. Additionally, by housing the radiation detector 10 in the housing 120 in a state where the reinforcing substrate 40 faces the irradiation surface 120A, the radiographic imaging apparatus 1 shown in FIG. 9B is manufactured.

In addition, the above step is an example, and for example, the step of connecting the flexible cable 112 described with reference to FIG. 10C to the sensor substrate 12 may be performed after the peeling step described with reference to FIG. 10E. That is, the sensor substrate 12 in a state where the flexible cable 112 is not connected to the terminal 113 may be peeled from the support body 400, and then the flexible cable 112 may be electrically connected to the terminal 113. Additionally, for example, the step of providing the reinforcing substrate 40 described with reference to FIG. 10D may be performed after the peeling step described with reference to FIG. 10E. That is, the sensor substrate 12 in a state where the reinforcing substrate 40 is not provided may be peeled from the support body 400, and then the reinforcing substrate 40 may be provided on the conversion layer 14. In addition, by providing the reinforcing substrate 40 on the sensor substrate 12 before the peeling step as in the above step, in the peeling step, the sensor substrate 12 in a state where the stiffness is reinforced by the reinforcing substrate 40 is peeled from the support body 400. For that reason, for example, it is possible to suppress the peeling of the conversion layer 14 from the base material 11 resulting from the deflection of the base material 11 in the peeling step.

Figure 11A:
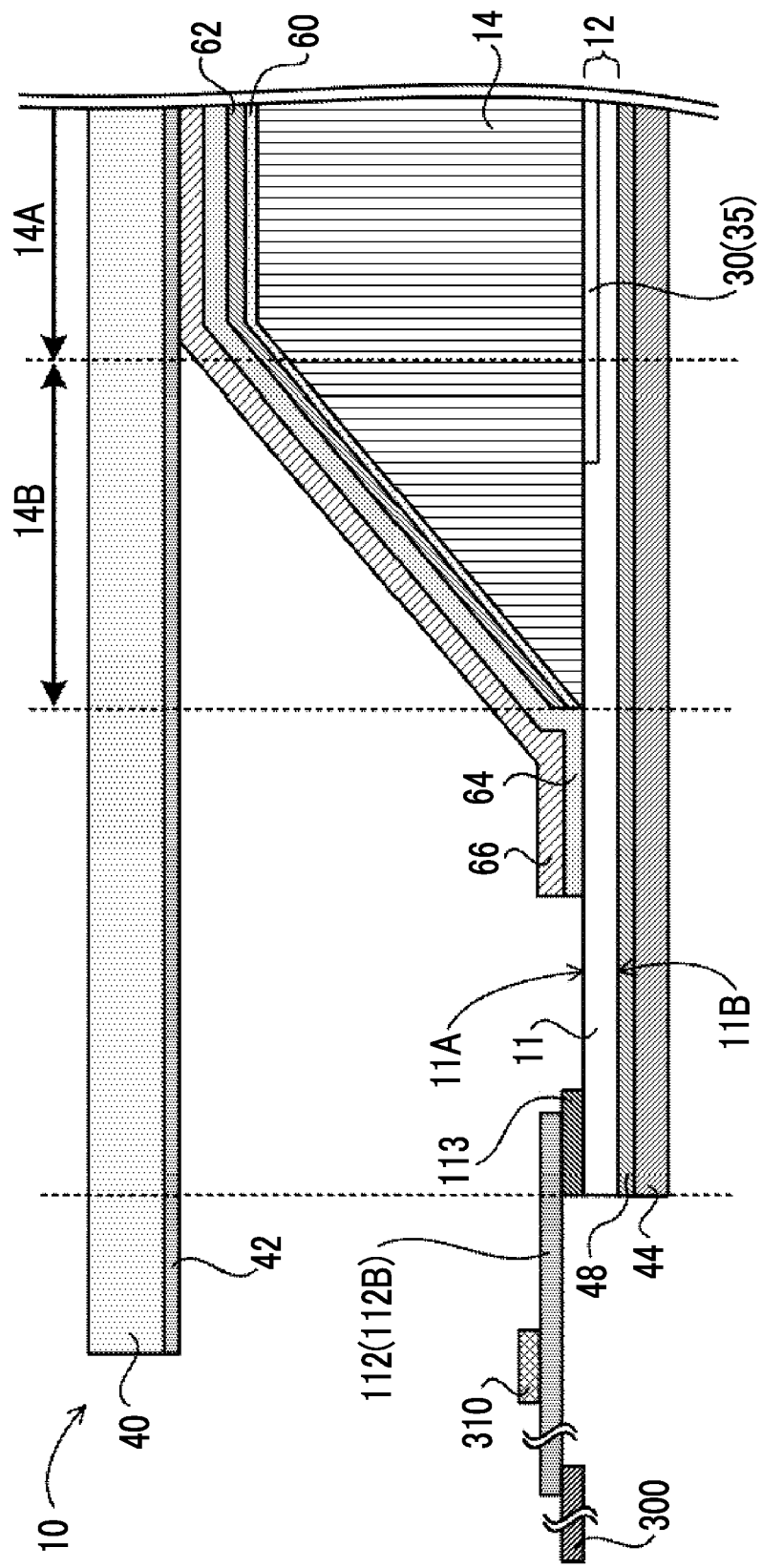
FIG. 11A is a cross-sectional view taken along line A-A of another example of a radiation detector of the embodiment.

In addition, in the above description, the size (area) of the reinforcing substrate 40 is the same as that of the base material 11 of the sensor substrate 12, but the size (area) of the reinforcing substrate 40 is not limited to the above-described configuration. For example, as shown in FIG. 11A, a configuration may be adopted in which the reinforcing substrate 40 is larger than the base material 11. In addition, the specific size of the reinforcing substrate 40 can be determined depending on the size of the inside of the housing 120 that houses the radiation detector 10, and the like. In the radiation detector 10 shown in FIG. 11A, the end part of the reinforcing substrate 40 is located outside an end part of the base material 11, that is, the sensor substrate 12.

In this way, by making the size of the reinforcing substrate 40 larger than the size of the base material 11, for example, for example, in a case where an impact is applied to the housing 120 and a side surface (a surface intersecting the irradiation surface 120A) of the housing 120 is recessed such that the radiographic imaging apparatus 1 is dropped, the reinforcing substrate 40 interferes with the side surface of the housing 120. On the other hand, since the sensor substrate 12 is smaller than the reinforcing substrate 40, the sensor substrate 12 is less likely to interfere with the side surface of the housing 120. Therefore, according to the radiation detector 10 shown in FIG. 11A, it is possible to suppress the influence of the impact applied to the radiographic imaging apparatus 1 on the sensor substrate 12.

In addition, from the viewpoint of suppressing the influence of the impact of the reinforcing substrate 40 applied to the radiographic imaging apparatus 1 on the sensor substrate 12, as shown in FIG. 11A, at least a part of the end part of the reinforcing substrate 40 may protrude further outward than the end part of the base material 11. For example, even in a case where the size of the reinforcing substrate 40 is smaller than the size of the base material 11, the end part of the reinforcing substrate 40 that protrudes further outward than the end part of the base material 11 interferes with the side surface of the housing 120. Therefore, the influence of the impact on the sensor substrate 12 can be suppressed.

Figure 11B:
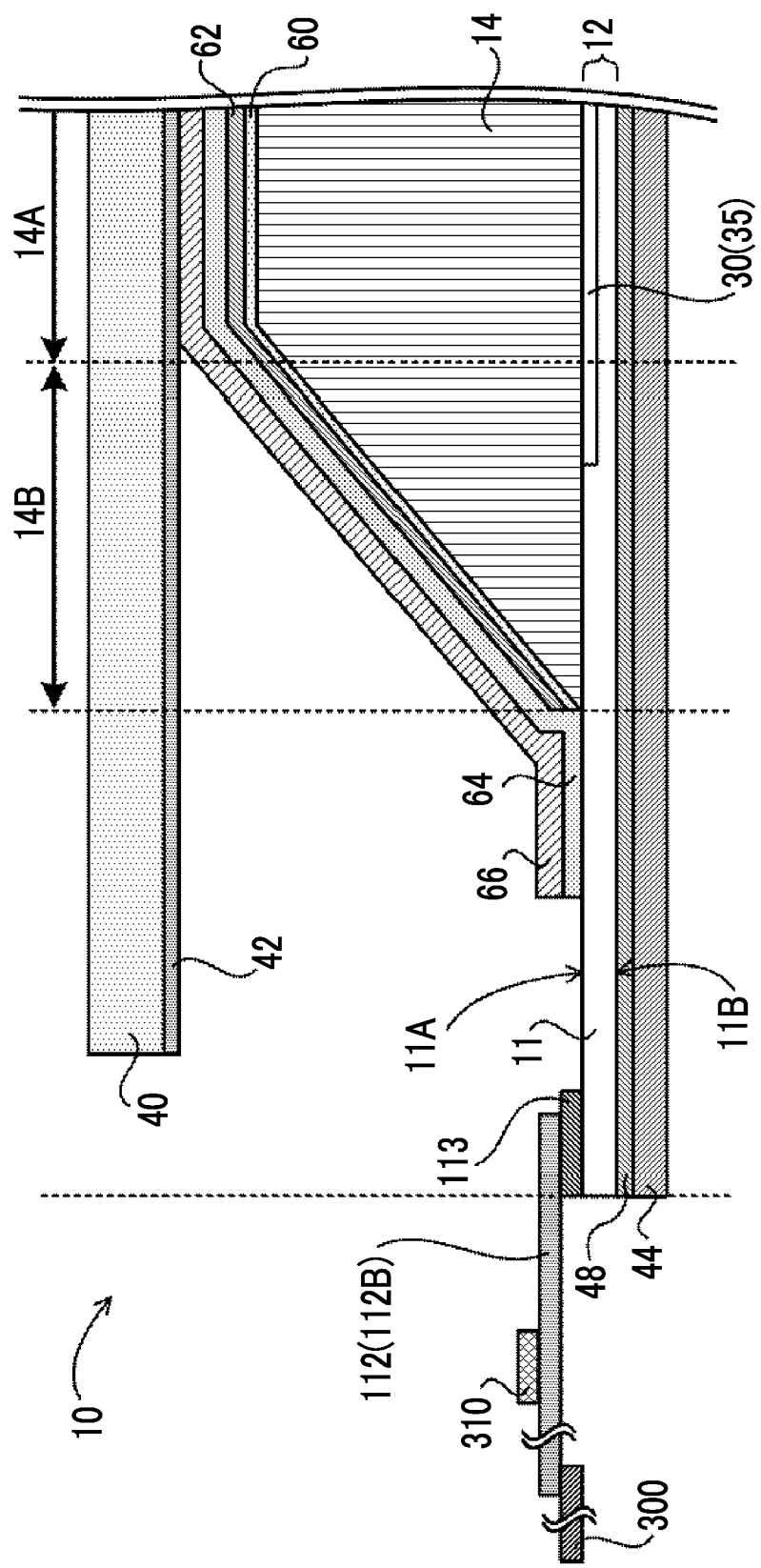
FIG. 11B is a cross-sectional view taken along line A-A of another example of a radiation detector of the embodiment.
Figure 11C:
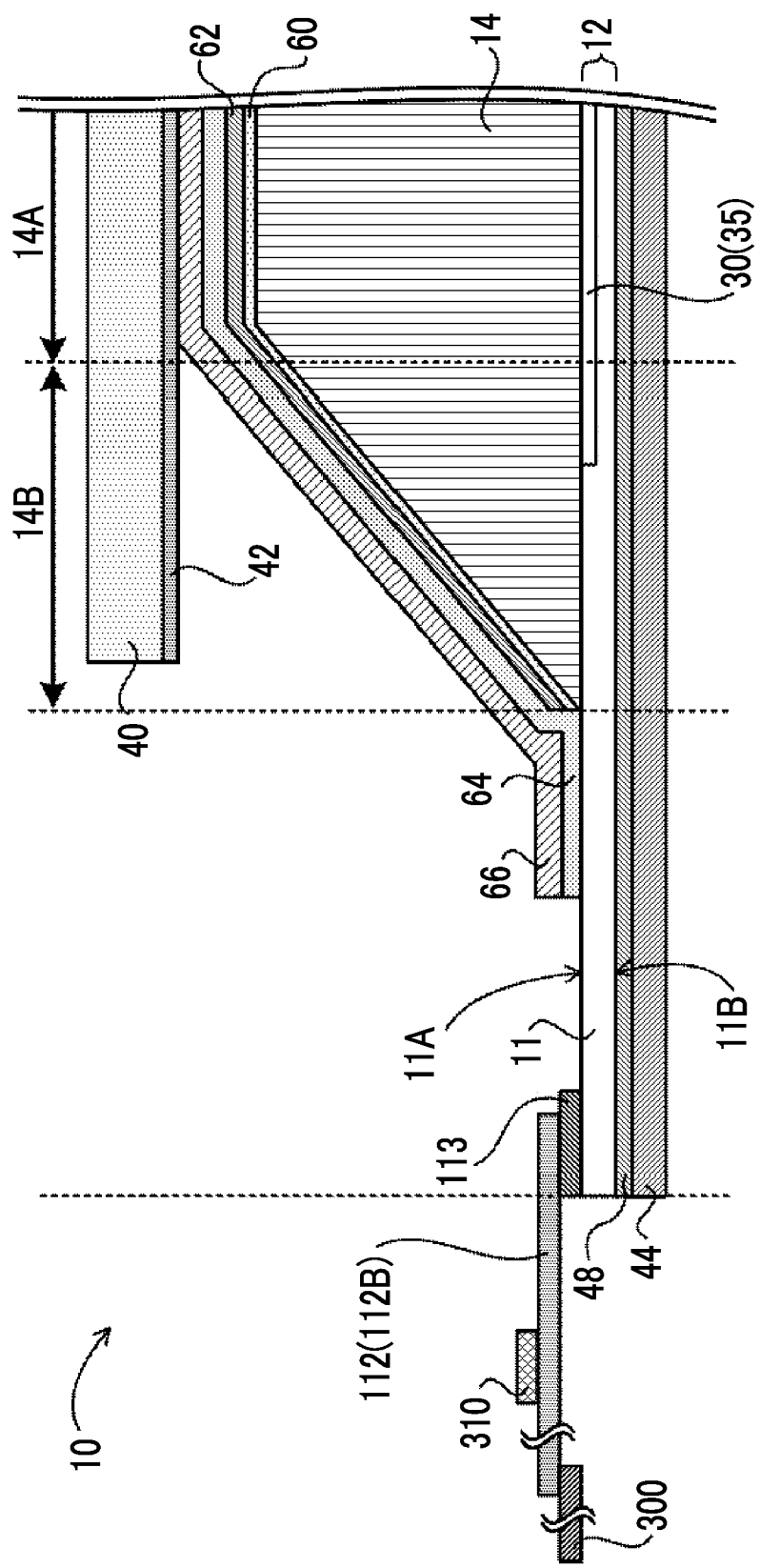
FIG. 11C is a cross-sectional view taken along line A-A of another example of a radiation detector of the embodiment.

Additionally, for example, as shown in FIGS. 11B and 11C, a configuration may be adopted in which the reinforcing substrate 40 is smaller than the base material 11. In the example shown in FIG. 11B, the reinforcing substrate 40 is not provided at the position facing the terminal 113. That is, the area of the reinforcing substrate 40 in the radiation detector 10 is smaller than a value obtained by subtracting the area of a region where the terminal 113 is provided from the area of the base material 11. On the other hand, in an example shown in FIG. 11C, the end part of the reinforcing substrate 40 is located at the peripheral edge part 14B of the conversion layer 14, and the conversion layer 14 is provided in a region narrower than a region where the reinforcing substrate 40 covers the entire first surface 11A of the base material 11.

Removing the flexible cable 112 or a component electrically connected to the base material 11 (sensor substrate 12) and newly reconnecting the component due to a defect or a positional deviation is referred to as rework. In this way, by making the size of the reinforcing substrate 40 smaller than the size of the base material 11, the rework can be performed without being disturbed by the end part of the reinforcing substrate 40. Therefore, the rework of the flexible cable 112 can be facilitated.

In addition, the configuration and manufacturing method of the radiographic imaging apparatus 1 and the radiation detector 10 are not limited to the above-described form. For example, the configurations shown in the following Modification Examples 1 to 7 may be used. In addition, configurations may be adopted in which the above-described form and respective Modification Examples 1 to 4 are combined appropriately, and the disclosure is not limited to Modification Examples 1 to 4.

Modification Example 1

In the present modification example, a configuration in which the reinforcing substrate 40 in the radiation detector 10 is supported by the support member 72 will be described with reference to FIGS. 12A and 12B. Each of FIGS. 12A and 12B shows an example of a cross-sectional view of a radiation detector 10 of the present modification example, which corresponds to the sectional view taken along the line A-A of the radiation detector 10 illustrated in FIG. 3.

Figure 12A:
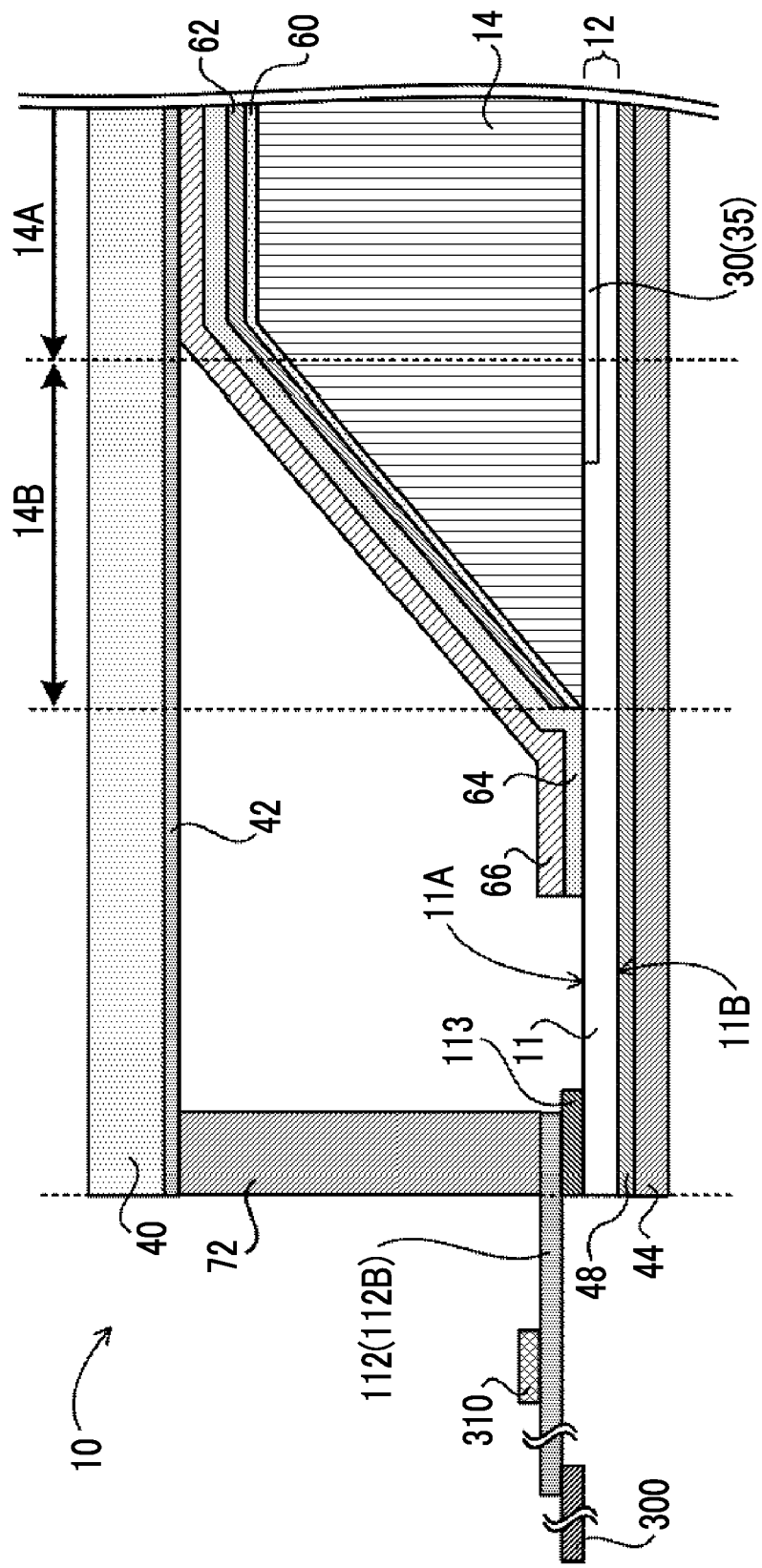
FIG. 12A is a cross-sectional view taken along line A-A of an example of a radiation detector of Modification Example 1.

In the radiation detector 10 shown in FIG. 12A, the end part of the reinforcing substrate 40 is supported by the support member 72. That is, one end of the support member 72 is connected to the flexible cable 112 or the first surface 11A of the base material 11, and the other end of the support member 72 is connected to the end part of the reinforcing substrate 40 by the pressure sensitive adhesive 42. In addition, the support member 72 may be provided on the entire outer edge part of the base material 11 or may be provided on a portion of the outer edge part. In this way, by supporting the end part of the reinforcing substrate 40 that extends while forming the space between the reinforcing substrate 40 and the base material 11 with the support member 72, the peeling of the conversion layer 14 from the sensor substrate 12 can be suppressed. Additionally, by providing the support member 72 on the flexible cable 112 connected to the terminal 113, it is possible to suppress the peeling of the flexible cable 112 from the terminal 113.

Figure 12B:
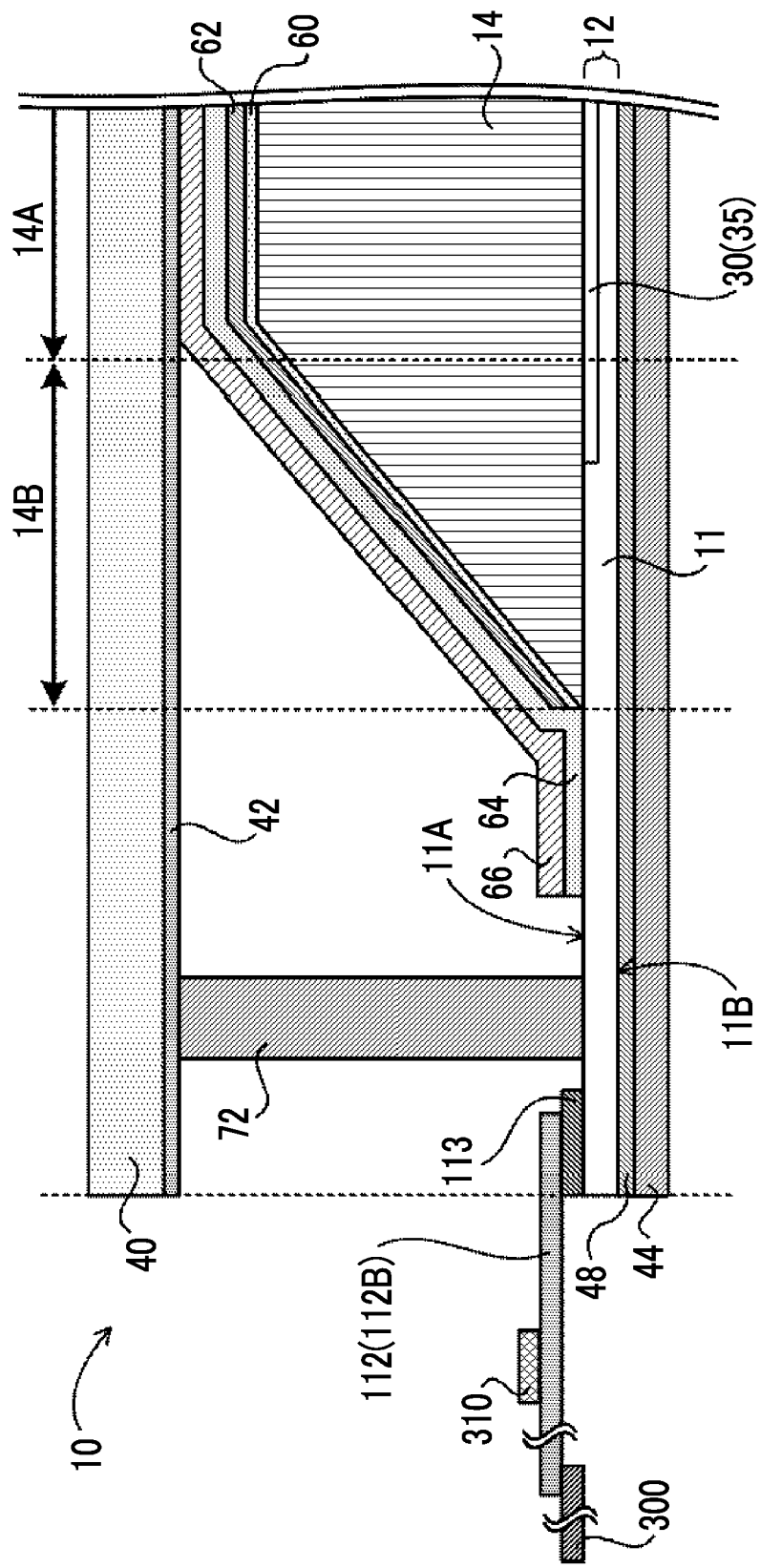
FIG. 12B is a cross-sectional view taken along line A-A of another example of a radiation detector of Modification Example 1.

On the other hand, in the radiation detector 10 shown in FIG. 12B, a position inside the end part of the reinforcing substrate 40 is supported by the support member 72. In the example shown in FIG. 12B, the position where the support member 72 is provided is only outside the region where the flexible cable 112 and the terminal 113 are provided. In the example shown in FIG. 12B, one end of the support member 72 is connected to the first surface 11A of the base material 11, and the other end of the support member 72 is connected to the end part of the reinforcing substrate 40 by the pressure sensitive adhesive 42. In this way, by not providing the support member 72 on the flexible cable 112 and the terminal 113, the rework of the flexible cable 112 can be facilitated.

In this way, according to the radiation detector 10 of the present modification example, by supporting the reinforcing substrate 40 with the support member 72, the stiffness reinforcing effect of the reinforcing substrate 40 can be obtained up to the vicinity of the end part of the base material 11, and the effect of suppressing the deflection of the material 11 can be exerted. For that reason, according to the radiation detector 10 of the present modification example, the peeling of the conversion layer 14 from the sensor substrate 12 can be suppressed.

Modification Example 2

In the present modification example, a configuration in which the periphery of the conversion layer 14 in the radiation detector 10 is sealed will be described with reference to FIG. 13. FIG. 13 shows an example of a cross-sectional view of a radiation detector 10 of the present modification example, which corresponds to the sectional view taken along the line A-A of the radiation detector 10 shown in FIG. 3.

As shown in FIG. 13, a configuration may be adopted in which the peripheral edge part 14B of the conversion layer 14 is sealed by a sealing member 70. In the example shown in FIG. 13, the sealing member 70 is provided in a space created by the base material 11, the conversion layer 14, and the reinforcing substrate 40 as described above. Specifically, a sealing member 70 is provided in a space formed between the conversion layer 14 (protective layer 66) and the reinforcing substrate 40 in the region corresponding to the peripheral edge part 14B of the conversion layer 14 and the region further outside thereof. The material of the sealing member 70 is not particularly limited, and for example, resin can be used.

The method of providing the sealing member 70 is not particularly limited. For example, the reinforcing substrate 40 may be provided on the conversion layer 14 covered with a pressure-sensitive adhesive layer 60, the reflective layer 62, the adhesive layer 64, and the protective layer 66 by the pressure sensitive adhesive 42, and then, the sealing member 70 having fluidity may be injected into the space formed between the conversion layer 14 (protective layer 66) and the reinforcing substrate 40 to cure the reinforcing substrate 40. Additionally, for example, after the conversion layer 14, the pressure-sensitive adhesive layer 60, the reflective layer 62, the adhesive layer 64, and the protective layer 66 are sequentially formed on the base material 11, the sealing member 70 may be formed, and the reinforcing substrate 60 may be provided by the pressure sensitive adhesive 42 in a state where the conversion layer 14 and the sealing member 70 covered with the pressure-sensitive adhesive layer 40, the reflective layer 62, the adhesive layer 64, and the protective layer 66.

Additionally, the region where the sealing member 70 is provided is not limited to the configuration shown in FIG. 13. For example, the sealing member 70 may be provided on the entire first surface 11A of the base material 11, and the terminal 113 to which the flexible cable 112 is electrically connected may be sealed together with the flexible cable 112.

In this way, by filling the space formed between the conversion layer 14 and the reinforcing substrate 40 with the sealing member 70 and sealing the conversion layer 14, the peeling of the reinforcing substrate 40 from the conversion layer 14 can be suppressed. Moreover, since the conversion layer 14 has a structure in which the conversion layer 14 is fixed to the sensor substrate 12 by both the reinforcing substrate 40 and the sealing member 70, the stiffness of the base material 11 is further reinforced.

In addition, in a case where the present modification example and the above Modification Example 1 are combined with each other, in other words, in a case where the radiation detector 10 comprises the sealing member 70 and the support member 72, a configuration may be adopted in which a part or the whole of the space surrounded by the support member 72, the reinforcing substrate 40, the conversion layer 14, and the base material 11 is filled with the sealing member 70 and may be sealed by the sealing member 70.

Modification Example 3

In the above-described configuration, the configuration in which the density of the plurality of through-holes 51 in the porous layer 50 is uniform has been described, but a configuration may be adopted in which the density of the plurality of through-holes 51 in the porous layer 50 is non-uniform. More specifically, the porous layer 50 may have different densities of through-holes 51 in each region of a plurality of regions lined up along the first surface 11A of the base material 11.

Since the porous layer 50 has a relatively higher thermal conductivity than the atmosphere, the smaller the density of the through-holes 51, the higher the thermal conductivity of the porous layer 50. For example, the circuit unit such as the signal processing substrate 300 tends to generate a larger heat generation amount than other components. For that reason, the density of the through-holes 51 in the porous layer 50 may be made smaller than other portions to increase the thermal conductivity in the vicinity of components that generate heat or at a position where the heat becomes high in the housing 120, or the like.

An example of the porous layer 50 in this case is shown in FIG. 14A. In the porous layer 50 shown in FIG. 14A, the density of the through-holes 51 in the region 52 corresponding to the position where the circuit unit is provided is smaller than the density of the through-holes 51 in the other regions 53.

In the radiation detector 10 shown in FIG. 14A, since the density of the through-holes 51 in the region 52 of the porous layer 50 is smaller than the density of the through-holes 51 in the other regions 53, the heat dissipation in the region 52 can be increased. For that reason, non-uniformity of the amount of heat in the housing 120 can be suppressed. For example, in a case where heat is transferred non-uniformly in a plane direction of the sensor substrate 12, there is a case where a dark current generated in the sensor unit 34 of each pixel 30 changes depending on the transferred heat, and image unevenness occurs in the radiographic image. In contrast, in the radiation detector 10 shown in FIG. 14A, since the thermal conductivity in the region 52 corresponding to a position where the heat generation amount is large can be increased, non-uniform transfer of heat in the plane direction of the sensor substrate 12 can be suppressed, and the image unevenness of the radiographic image can be suppressed.

On the other hand, the weight of the porous layer 50 can be reduced as the density of the through-holes 51 increases. Depending on the disposition of the components in the housing 120, there is a case where it is difficult to make the weight balance of the entire housing 120 uniform. For example, the power source unit 108 tends to be heavier than other components. For that reason, in the vicinity of heavy components or the like, the density of the through-holes 51 in the porous layer 50 may be made smaller than the other portions, and the weight of the through-hole portion may be lightened.

Figure 14B:
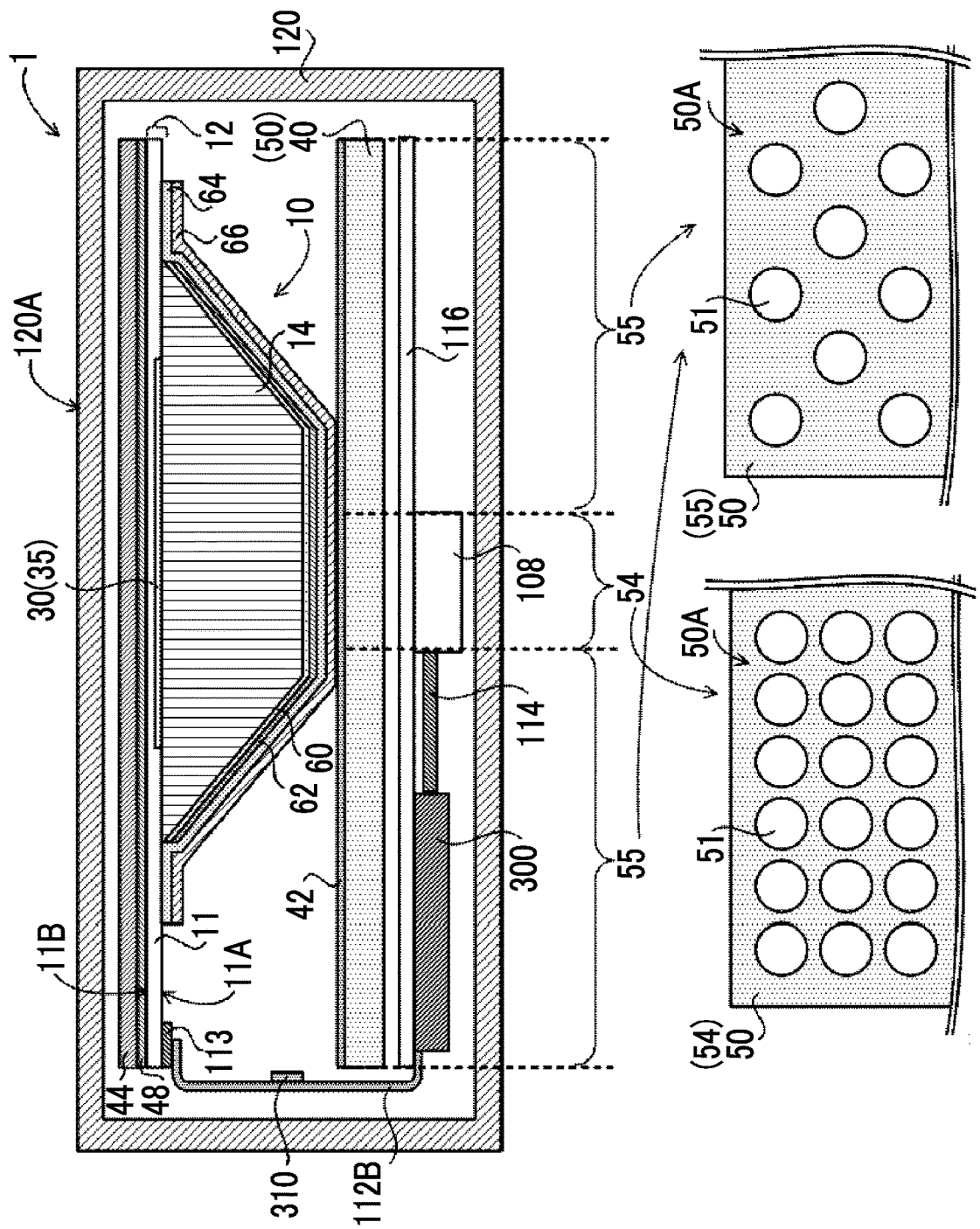
FIG. 14B is a diagram for explaining another example of the porous layer of Modification Example 3.

An example of the porous layer 50 in this case is shown in FIG. 14B. In the porous layer 50 shown in FIG. 14B, the density of the through-holes 51 in the region 54 corresponding to a position where the power source unit 108 is provided is higher than the density of the through-holes 51 in the other regions 55.

In the radiation detector 10 shown in FIG. 14B, since the density of the through-holes 51 in the region 54 of the porous layer 50 is higher than the density of the through-holes 51 in the other region 55, the weight of the region 54 can be reduced compared to that of the other region 55. For that reason, in the radiation detector 10 shown in FIG. 14B, the weight balance of the entire housing 120 can be adjusted, and the usability of the radiographic imaging apparatus 1 can be improved.

Modification Example 4

In the present modification example, a modification example of the radiographic imaging apparatus 1 will be described with reference to FIGS. 15A to 15C. Each of FIGS. 15A to 15C is an example of cross-sectional views of a radiographic imaging apparatus 1 of the present modification example.

Figure 15A:
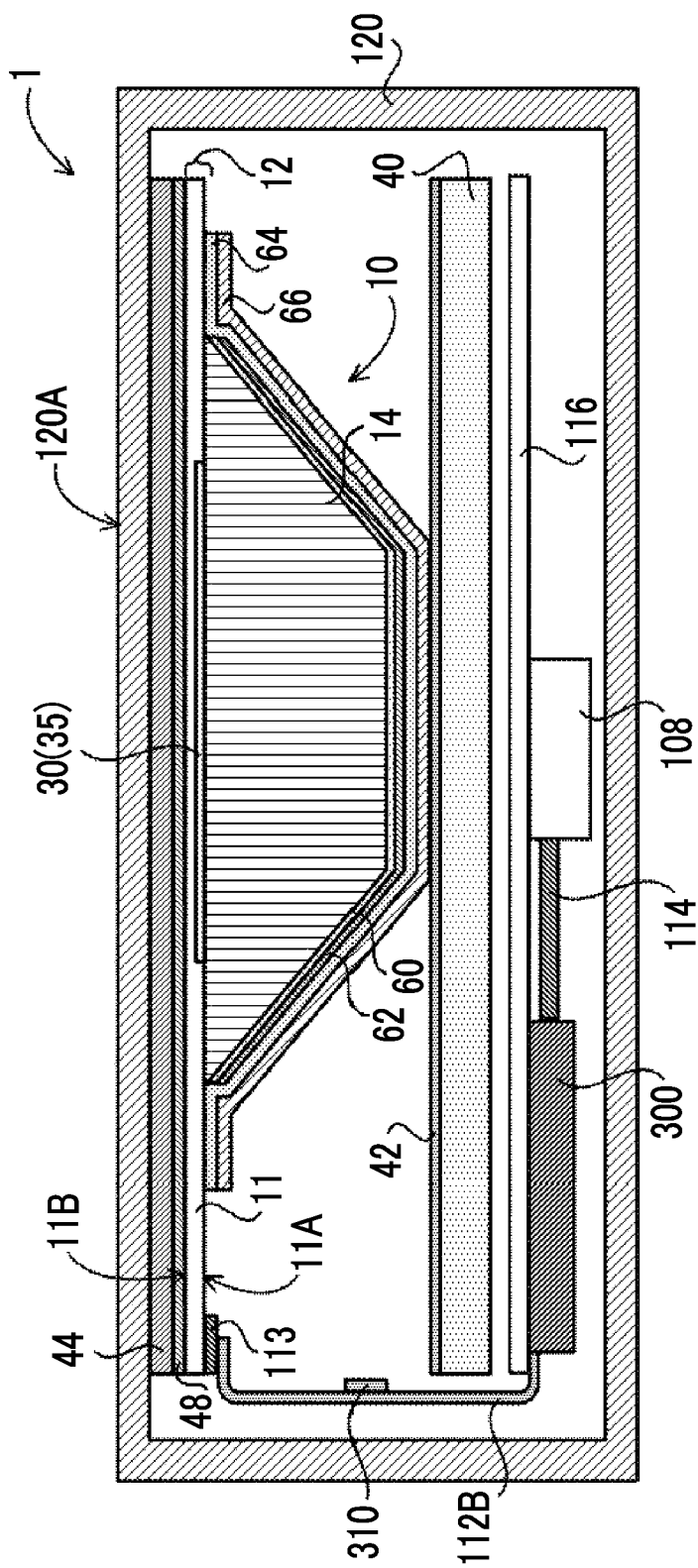
FIG. 15A is a cross-sectional view of an example of a radiographic imaging apparatus of Modification Example 4.

FIG. 15A shows an example of the ISS type radiographic imaging apparatus 1 in which the radiation detector 10 is in contact with the inner wall surface of the top plate on the irradiation surface 120A side of the housing 120. In the example shown in FIG. 15A, the electromagnetic shield layer 44 is in contact with the inner wall surface of the top plate on the irradiation surface 120A side of the housing 120. In this case, the radiation detector 10 and the inner wall surface of the housing 120 may be bonded to each other via an adhesive layer, or may simply be in contact with each other without an adhesive layer. Since the radiation detector 10 and the inner wall surface of the housing 120 are in contact with each other in this way, the stiffness of the radiation detector 10 is further secured.

Figure 15B:
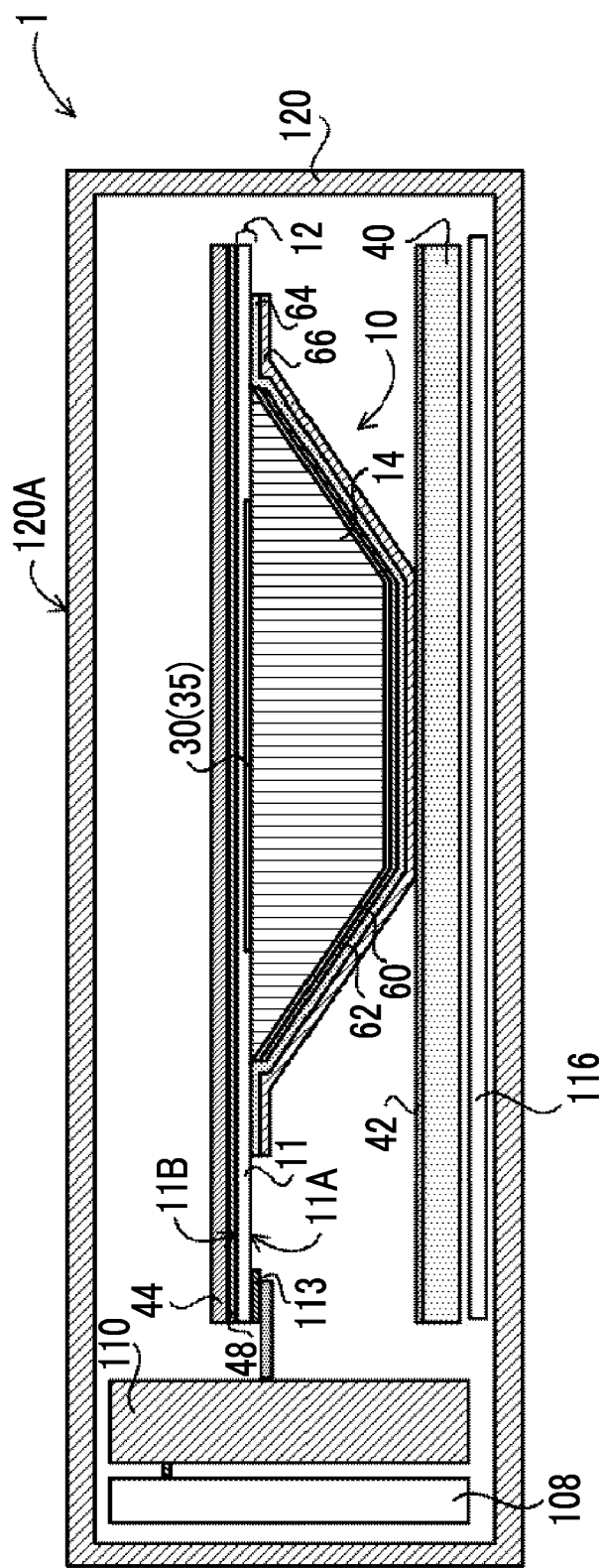
FIG. 15B is a cross-sectional view of another example of the radiographic imaging apparatus of Modification Example 4.
Figure 15C:
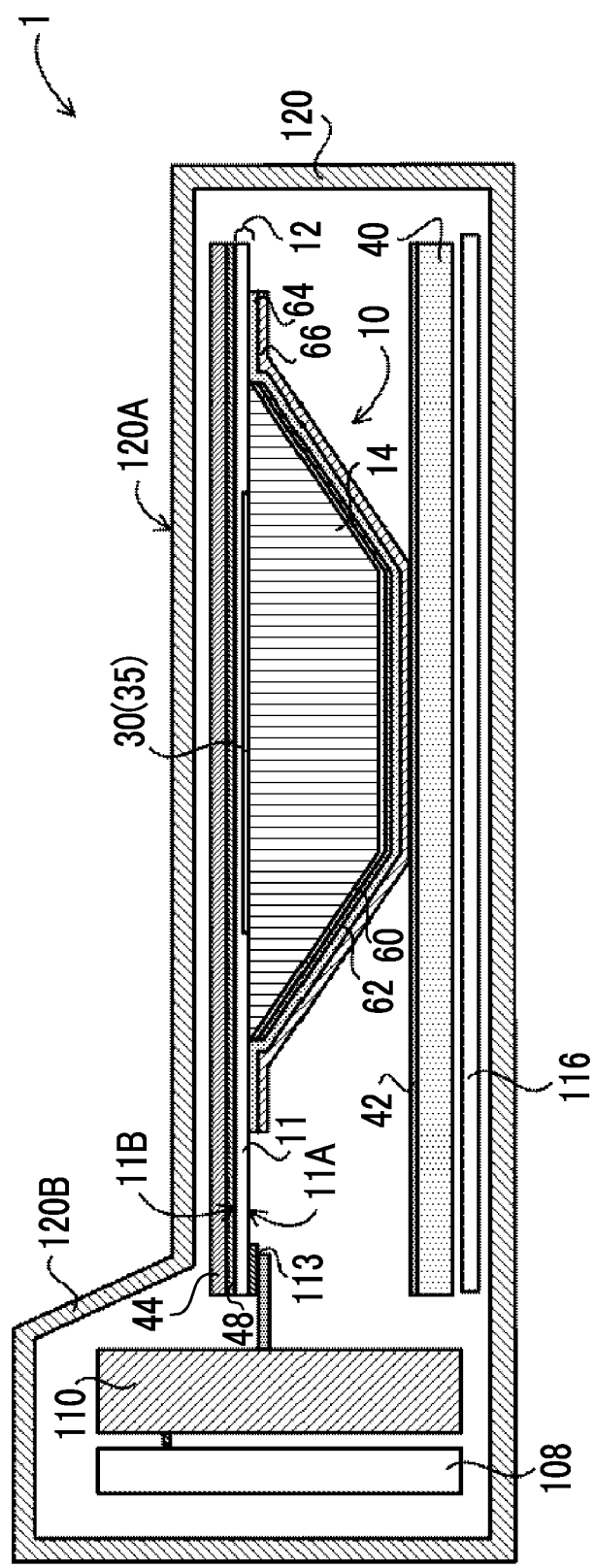
FIG. 15C is a cross-sectional view of still another example of the radiographic imaging apparatus of Modification Example 4.

Additionally, FIG. 15B shows an example of an ISS type radiographic imaging apparatus 1 in which circuit units such as the radiation detector 10, the control substrate 110, and the power source unit 108 are juxtaposed in the transverse direction in the drawing. In other words, in the radiographic imaging apparatus 1 shown in FIG. 15B, the radiation detector 10 and the circuit unit are disposed side by side in a direction intersecting the irradiation direction of the radiation.

In addition, although FIG. 15B shows a configuration in which both the power source unit 108 and the control substrate 110 are provided on one side of the radiation detector 10, specifically, on one side of a rectangular pixel region 35, a position where the circuit units such as the power source unit 108 and the control substrate 110 are provided is not limited to the configuration shown in FIG. 15B. For example, the circuit units such as the power source unit 108 and the control substrate 110 may be provided so as to be respectively distributed onto two facing sides of the pixel region 35 or may be provided so as to be respectively distributed onto two adjacent sides. In this way, by disposing the radiation detector 10 and the circuit unit side by side in the direction intersecting the irradiation direction of the radiation, the thickness of the housing 120, more specifically, the thickness in the direction in which the radiation is transmitted can be further reduced, and the radiographic imaging apparatus 1 can be slimmed.

Additionally, in a case where the radiation detector 10 and the circuit unit are disposed side by side in a direction intersecting the radiation irradiation direction, the thickness of the housing 120 may be different between the portion of the housing 120 in which each of the circuit units such as the power source unit 108 and a control substrate 110 are provided and the portion of the housing 120 in which the radiation detector 10 is provided, as in the radiographic imaging apparatus 1 shown in FIG. 15C.

As shown in the example shown in FIGS. 15B and 15C, there are many cases where the circuit units of the power source unit 108 and the control substrate 110 are thicker than the radiation detector 10. In such a case, as in the example shown in FIG. 15C, the thickness of the portion of the housing 120 in which the radiation detector 10 is provided may be smaller than the thickness of the portion of the housing 120 in which each of the circuit units such as the power source unit 108 and the control substrate 110 is provided. According to the radiographic imaging apparatus 1 shown in FIG. 15C, it is possible to configure an ultra-thin radiographic imaging apparatus 1 according to the thickness of the radiation detector 10.

In addition, as in the example shown in FIG. 15C, in a case where the thickness of the portion of the housing 120 in which each of the circuit units such as the power source unit 108 and the control substrate 110 is provided and the thickness of the portion of the housing 120 in which the radiation detector 10 is provided are made different, and in a case where a step is generated at a boundary portion between the two portions, there is a concern that a sense of discomfort may be given to a subject who comes into contact with a boundary portion 120B. For that reason, it is preferable that the form of the boundary portion 120B has an inclination. Additionally, the portion of the housing 120 in which each of the circuit units such as the power source unit 108 and the control substrate 110 is housed and the portion of the housing 120 in which the radiation detector 10 is housed may be formed of different materials.

As described above, each of the above radiation detectors 10 comprises the sensor substrate 12, the conversion layer 14, and the reinforcing substrate 40. In the sensor substrate 12, the pixel region 35 of the flexible base material 11 is formed with the plurality of pixels 30 for accumulating the electric charges generated in response to the light converted from radiation. The conversion layer 14 is provided on the first surface 11A of the base material 11 on which the pixels 30 are provided and converts radiation into light. The reinforcing substrate 40 is provided on the surface of the conversion layer 14 opposite to the surface on the base material 11 side and includes the porous layer 50 having the plurality of through-holes 51 to reinforce the stiffness of the base material 11.

Therefore, in each of the above-described radiation detectors 10, the bending stiffness is high and the heat resistance can be improved. In particular, in the ISS type radiographic imaging apparatus 1, the above effects can be obtained while suppressing the influence of the through-holes 51 of the porous layer 50 of the reinforcing substrate 40 on the radiographic image.

In addition, the configurations of the radiographic imaging apparatus 1 and the radiation detector 10, and the method of manufacturing the radiation detector 10 are not limited to the configurations described with reference to FIGS. 1 to 15C. For example, although the configuration in which the reinforcing substrate 40 includes only the porous layer 50 has been described above, the reinforcing substrate 40 may include members other than the porous layer 50. For example, the reinforcing substrate 40 may include a laminated body in which the porous layer 50 and a rigid plate made of CFRP or the like are laminated. Additionally, in each of the above radiation detectors 10, the configuration in which the reinforcing substrate 40 is provided on the upper side of the conversion layer 14 has been described, but the reinforcing substrate 40 may also be provided on the second surface 11B side of the base material 11. For example, the reinforcing substrate 40 may be bonded to the electromagnetic shield layer 44. Additionally, a rigid plate made of CFRP or the like for reinforcing the stiffness of the base material 11 may be provided on the second surface 11B of the base material 11.

Additionally, for example, as shown in FIG. 1, an aspect in which the pixels 30 are two-dimensionally arranged in a matrix has been described. However, the disclosure is not limited, and the pixels 30 may be one-dimensionally arranged or may be arranged in a honeycomb arrangement. Additionally, the shape of the pixels is also not limited, and may be a rectangular shape, or may be a polygonal shape, such as a hexagonal shape. Moreover, the shape of the pixel region 35 is also not limited.

In addition, the configurations, manufacturing methods, and the like of the radiographic imaging apparatuses 1, the radiation detectors 10, and the like in the above embodiments and respective modification examples are merely examples, and can be modified depending on situations without departing from the scope of the present disclosure.

The disclosure of Japanese Patent Application No. 2020-038171 filed on Mar. 5, 2020 is incorporated in the present specification by reference in its entirety.

All documents, patent applications, and technical standards described in the present specification are incorporated in the present specification by reference in their entireties to the same extent as in a case where the individual documents, patent applications, and technical standards are specifically and individually written to be incorporated by reference.

What is claimed is:

1. A radiation detector comprising:
a substrate in which a plurality of pixels for accumulating electric charges generated in response to light converted from radiation are formed in a pixel region of a flexible base material;
a conversion layer that is provided on a surface side of the base material provided with the pixels and converts the radiation into the light; and
a reinforcing substrate that is provided on a surface of the conversion layer opposite to a surface on a base material side and includes a porous layer having a plurality of through-holes to reinforce a stiffness of the base material,
wherein the porous layer has a porous structure having a porosity of 15% or more and 50% or less and a pore diameter of 0.3 µm or more and 5 mm or less.

2. The radiation detector according to claim 1, wherein each of the plurality of through-holes has an opening diameter of 0.5 mm or more and 50 mm or less, a pitch of 1 mm or more and 50 mm or less, and an opening ratio of 10% or more and 50% or less.

3. The radiation detector according to claim 1, wherein the porous layer has the plurality of through-holes having a hexagonal opening.

4. The radiation detector according to claim 3, wherein the porous layer has a honeycomb structure.

5. The radiation detector according to claim 1, wherein the porous layer has a flute structure in which an extension direction of a flute is an in-plane direction of the reinforcing substrate.

6. The radiation detector according to claim 5, wherein a pitch of the flute structure is at least a thickness of the flute structure and no more than three times the thickness.

7. The radiation detector according to claim 1, wherein a material of the porous layer includes at least one of carbon fiber reinforced plastic (CFRP), carbon fiber reinforced thermo plastics (CFRTP), polyvinyl chloride (PVC), polyethylene terephthalate (PET), polypropylene (PP), polyethylene (PE), aluminum, or magnesium.

8. The radiation detector according to claim 1, wherein a material of the porous layer includes carbon fiber reinforced plastic (CFRP).

9. The radiation detector according to claim 1, wherein the through-holes of the porous layer have different densities in each region of a plurality of regions lined up along the surface of the base material provided with the pixels.

10. The radiation detector according to claim 9, wherein the density of the through-holes in a region corresponding to a position where a circuit unit for reading the electric charges accumulated in the pixels is provided is smaller than the densities of the through-holes in the other regions.

11. The radiation detector according to claim 9, wherein the density of the through-holes in a region corresponding to a power source unit that supplies power to a circuit unit for reading the electric charges accumulated in the pixels is provided is larger than the densities of the through-holes in the other regions.

12. The radiation detector according to claim 1,
wherein the reinforcing substrate includes a laminated body in which a plurality of the porous layers are laminated.

13. The radiation detector according to claim 1,
wherein the porous layer has a protective plate provided on at least one surface of a surface on a conversion layer side and a surface opposite to the conversion layer.

14. The radiation detector according to claim 1, further comprising:
an antistatic layer that is provided on a surface of the base material opposite to the surface provided with the pixels.

15. The radiation detector according to claim 14,
wherein the antistatic layer is a laminated film of a resin film and a metal film.

16. A radiographic imaging apparatus comprising:
the radiation detector according to claim 1; and
a circuit unit for reading out the electric charges accumulated in the plurality of pixels.

17. A method of manufacturing a radiation detector, the method comprising:
providing a flexible base material on a support body and forming a substrate in which a plurality of pixels that accumulate electric charges generated in response to light converted from radiation are provided in a pixel region of a first surface of the base material;
providing a conversion layer that converts the radiation into the light on a surface side of the base material provided with the pixels;
providing a reinforcing substrate including a porous layer having a plurality of through-holes on a surface of the conversion layer opposite to a surface on a base material side to reinforce a stiffness of the base material; and
peeling the substrate from the support body.

18. The method of manufacturing a radiation detector according to claim 17,
wherein the substrate is peeled from the support body after the reinforcing substrate is provided on the substrate.

* * * * *